(12) United States Patent
Athos et al.

(10) Patent No.: US 11,723,712 B2
(45) Date of Patent: Aug. 15, 2023

(54) HIGH-VOLTAGE ANALOG CIRCUIT PULSER AND PULSE GENERATOR DISCHARGE CIRCUIT

(71) Applicant: Pulse Biosciences, Inc., Hayward, CA (US)

(72) Inventors: Brian G. Athos, San Francisco, CA (US); Darrin R. Uecker, San Mateo, CA (US); Shu Xiao, Norfolk, VA (US)

(73) Assignee: Pulse Biosciences, Inc., Hayward, CA (US)

( * ) Notice: Subject to any disclaimer, the term of this patent is extended or adjusted under 35 U.S.C. 154(b) by 226 days.

(21) Appl. No.: 17/083,012

(22) Filed: Oct. 28, 2020

(65) Prior Publication Data

US 2021/0038282 A1 Feb. 11, 2021

Related U.S. Application Data

(60) Division of application No. 15/347,729, filed on Nov. 9, 2016, now Pat. No. 10,874,451, which is a
(Continued)

(51) Int. Cl.
*A61B 18/14* (2006.01)
*A61B 18/12* (2006.01)
(Continued)

(52) U.S. Cl.
CPC ............ *A61B 18/1206* (2013.01); *A61N 1/32* (2013.01); *H03K 3/57* (2013.01);
(Continued)

(58) Field of Classification Search
CPC .......... A61B 2018/00613; A61B 2018/00773; A61B 2018/00791; A61B 2018/00827;
(Continued)

(56) References Cited

U.S. PATENT DOCUMENTS 1,070,914 A 8/1913 Raveling et al.
5,568,035 A * 10/1996 Kato ....................... H02M 3/07
363/59
(Continued)

FOREIGN PATENT DOCUMENTS

EP 2160992 A2 3/2010
JP 01066985 3/1989
(Continued)

OTHER PUBLICATIONS

KR-10-2018-7025718-KIPO-200629-Office Action English Translation (7-pages).
(Continued)

*Primary Examiner* — Joanne M Rodden
*Assistant Examiner* — Sean W Collins

(57) ABSTRACT

A pulse generator discharge circuit is disclosed. The circuit includes one or more discharge stages, each discharge stage including a plurality of control input terminals. The circuit also includes first and second discharge terminals, and a plurality of serially connected switches electrically connected between the first and second discharge terminals, where a conductive state of each of the switches is controlled by a control signal. The circuit also includes a plurality of inductive elements configured to generate the control signals for the serially connected switches, where each inductive element is configured to generate a control signal for one of the serially connected switches in response to one or more input signals at one or more of the control input terminals, and where each of the serially connected switches is configured to receive a control signal from a respective one of the inductive elements.

23 Claims, 26 Drawing Sheets

Related U.S. Application Data continuation-in-part of application No. 15/148,344, filed on May 6, 2016, now Pat. No. 10,548,665.

(60) Provisional application No. 62/301,477, filed on Feb. 29, 2016.

(51) Int. Cl.
  *H03K 3/57* (2006.01)
  *A61N 1/32* (2006.01)
  *A61B 18/00* (2006.01)
  *A61N 1/40* (2006.01)

(52) U.S. Cl.
  CPC ............... *A61B 2018/00291* (2013.01); *A61B 2018/00577* (2013.01); *A61B 2018/00642* (2013.01); *A61B 2018/00714* (2013.01); *A61B 2018/00791* (2013.01); *A61B 2018/00827* (2013.01); *A61B 2018/00875* (2013.01); *A61B 2018/00892* (2013.01); *A61B 2018/143* (2013.01); *A61B 2018/1467* (2013.01); *A61N 1/40* (2013.01)

(58) Field of Classification Search
  CPC .......... A61B 2018/00892; A61N 1/327; H03K 3/57; H03K 7/08; H03K 17/063; H03K 17/74
  USPC ............. 307/108; 323/251; 331/6; 315/5.39, 315/5.45
  See application file for complete search history.

(56) References Cited

U.S. PATENT DOCUMENTS

| | | | |
|---|---|---|---|
| 5,635,776 A * | 6/1997 | Imi | H02M 3/07 307/108 |
| 5,774,348 A | 6/1998 | Druce et al. | |
| 5,902,272 A | 5/1999 | Eggers et al. | |
| 5,907,484 A | 5/1999 | Kowshik et al. | |
| 6,008,690 A | 12/1999 | Takeshima et al. | |
| 6,017,354 A | 1/2000 | Culp et al. | |
| 6,026,003 A | 2/2000 | Moore et al. | |
| 6,048,789 A | 4/2000 | Vines et al. | |
| 6,137,276 A | 10/2000 | Rudolph | |
| 6,190,381 B1 | 2/2001 | Olsen et al. | |
| 6,326,177 B1 | 12/2001 | SchoentJach et al. | |
| 6,831,377 B2 | 12/2004 | Yampolsky et al. | |
| 6,911,848 B2 | 6/2005 | Vinciarelli | |
| 7,209,373 B2 | 4/2007 | Oicles et al. | |
| 7,496,401 B2 | 2/2009 | Bernabei | |
| 7,767,433 B2 | 8/2010 | Kuthi et al. | |
| 7,855,904 B2 | 12/2010 | Kirbie et al. | |
| 7,937,143 B2 | 5/2011 | Demarais et al. | |
| 3,000,813 A1 | 8/2011 | Schoenbach et al. | |
| 8,512,334 B2 | 8/2013 | Nuccitelli et al. | |
| 8,688,227 B2 | 4/2014 | Nuccitelli et al. | |
| 8,822,222 B2 | 9/2014 | Beebe | |
| 9,101,337 B2 | 8/2015 | Hoegerle et al. | |
| 9,101,764 B2 | 8/2015 | Nuccitelli et al. | |
| 9,168,373 B2 | 10/2015 | Nuccitelli et al. | |
| 9,724,155 B2 | 8/2017 | Nuccitelli et al. | |
| 9,918,790 B2 | 3/2018 | Zemlin et al. | |
| 10,097,085 B2 | 10/2018 | Cadilhon et al. | |
| 10,252,050 B2 | 4/2019 | Kreis et al. | |
| 2001/0025177 A1 | 9/2001 | Woloszko et al. | |
| 2002/0049473 A1 * | 4/2002 | Irnich | A61N 1/3956 607/5 |
| 2002/0193833 A1 | 12/2002 | Dimmer et al. | |
| 2003/0204161 A1 | 10/2003 | Ferek-Petric | |
| 2003/0233087 A1 | 12/2003 | Chen et al. | |
| 2004/0080964 A1 | 4/2004 | Buchmann | |
| 2004/0240241 A1 | 12/2004 | Chueh et al. | |
| 2006/0062074 A1 | 3/2006 | Gundersen et al. | |
| 2006/0079886 A1 | 4/2006 | Orszulak et al. | |
| 2006/0090723 A1 | 5/2006 | Stuart | |
| 2006/0139977 A1 | 6/2006 | Oicles et al. | |
| 2007/0066957 A1 | 3/2007 | Demarais et al. | |
| 2007/0129626 A1 | 6/2007 | Mahesh et al. | |
| 2008/0077189 A1 | 3/2008 | Ostroff et al. | |
| 2008/0031337 A1 | 9/2008 | Krishnaswamy et al. | |
| 2008/0231337 A1 | 9/2008 | Krishnaswamy et al. | |
| 2009/0065444 A1 * | 3/2009 | Alley | B01D 61/025 210/243 |
| 2009/0198231 A1 | 8/2009 | Esser et al. | |
| 2009/0299362 A1 | 12/2009 | Long et al. | |
| 2010/0036284 A1 | 2/2010 | Laynes et al. | |
| 2010/0038971 A1 | 2/2010 | Sanders et al. | |
| 2010/0042095 A1 | 3/2010 | Frovato et al. | |
| 2010/0063496 A1 | 3/2010 | Travato et al. | |
| 2010/0240995 A1 | 9/2010 | Nuccitelli | |
| 2010/0318082 A1 | 12/2010 | Nuccitelli et al. | |
| 2010/0331758 A1 | 12/2010 | Davalos et al. | |
| 2011/0015630 A1 | 1/2011 | Azure | |
| 2011/0118729 A1 | 5/2011 | Heeren et al. | |
| 2011/0144641 A1 | 6/2011 | Dimalanta et al. | |
| 2011/0160514 A1 | 6/2011 | Long et al. | |
| 2011/0270249 A1 | 11/2011 | Utley et al. | |
| 2012/0223583 A1 * | 9/2012 | Cooley | H02J 3/381 327/109 |
| 2012/0277763 A1 | 11/2012 | Greenblatt et al. | |
| 2012/0310230 A1 | 12/2012 | Willis et al. | |
| 2012/0315704 A1 | 12/2012 | Beebe et al. | |
| 2013/0018441 A1 | 1/2013 | Childs | |
| 2013/0041443 A1 | 2/2013 | Weissberg et al. | |
| 2013/0150935 A1 | 6/2013 | Weissberg et al. | |
| 2013/0267943 A1 * | 10/2013 | Hancock | H05B 6/806 606/33 |
| 2013/0302409 A1 | 11/2013 | Fuchs et al. | |
| 2013/0345697 A1 | 12/2013 | Fuchs et al. | |
| 2014/0046322 A1 | 2/2014 | Callas et al. | |
| 2014/0052126 A1 | 2/2014 | Long et al. | |
| 2014/0081256 A1 | 3/2014 | Carmel et al. | |
| 2014/0228835 A1 | 8/2014 | Mielekamp et al. | |
| 2014/0277219 A1 | 9/2014 | Nanda | |
| 2014/0336638 A1 | 11/2014 | Deem et al. | |
| 2014/0358066 A1 | 12/2014 | Nuccitelli et al. | |
| 2015/0032100 A1 | 1/2015 | Coulson et al. | |
| 2015/0065946 A1 | 3/2015 | Gehl et al. | |
| 2015/0272657 A1 | 10/2015 | Yates et al. | |
| 2016/0066977 A1 | 3/2016 | Neal, II et al. | |
| 2017/0033686 A1 | 2/2017 | Cadilhon et al. | |
| 2017/0245928 A1 | 8/2017 | Xiao et al. | |
| 2017/0246455 A1 | 8/2017 | Athos et al. | |
| 2017/0319851 A1 | 11/2017 | Athos et al. | |
| 2017/0326361 A1 | 11/2017 | Kreis | |
| 2017/0360504 A1 | 12/2017 | Nuccitelli et al. | |
| 2018/0078755 A1 | 3/2018 | Kreis | |
| 2018/0110557 A1 | 4/2018 | Muratori et al. | |
| 2018/0154142 A1 | 6/2018 | Guo et al. | |
| 2019/0046791 A1 | 2/2019 | Ebbers et al. | |
| 2019/0217080 A1 | 7/2019 | Moss et al. | |

FOREIGN PATENT DOCUMENTS

| | | |
|---|---|---|
| JP | 1066985 A | 3/1989 |
| JP | H1064691 A | 3/1998 |
| JP | 2009-90113 A | 4/2009 |
| WO | 2005115536 A1 | 12/2005 |
| WO | 2007030415 A1 | 3/2007 |
| WO | 2008034103 A1 | 3/2008 |
| WO | 2011109141 A1 | 9/2011 |
| WO | 2011146498 A2 | 11/2011 |
| WO | 2012076844 A1 | 6/2012 |
| WO | 2014060854 A1 | 4/2014 |
| WO | 2016089781 A1 | 6/2016 |
| WO | 2017/151260 A1 | 9/2017 |
| WO | 2017/151261 A1 | 9/2017 |
| WO | 2017200954 A1 | 11/2017 |
| WO | 2017201394 A1 | 11/2017 |
| WO | 2018053539 A1 | 3/2018 |

(56) References Cited

FOREIGN PATENT DOCUMENTS

WO     2018075946 A1    4/2018
WO     2018089506 A1    5/2018

OTHER PUBLICATIONS

European Application No. 17760443.6, Extended European Search Report and Opinion, dated Nov. 11, 2019, 6 pages.
Grekhov et al., "High-Power Semiconductor-Based Nano and Subnanosecond Pulse Generator With a Low Delay Time," IEEE Transactions On Plasma Science, Aug. 2005, vol. 33, No. 4, pp. 1240-1244.
Australian Application No. 2017225296, Examination Report dated Nov. 1, 2019, 5 pages.
Canadian Application No. 3,015,754, Office Action dated Sep. 11, 2019, 4 pages.
Japanese Application No. 2018-544079, Notice of Rejection dated Aug. 13, 2019, 6 pages.
U.S. Appl. No. 15/148,344, Non-final Office Action dated Feb. 7, 2019, 12 pages.
U.S. Appl. No. 15/148,344, Final Office Action dated Aug. 9, 2019, 14 pages.
Anand et al., "Adaptive Immune Response to Nano-Pulse Stimulation (NPS), Nov. 11, 2016, Poster presentation at the 31st Annual Meeting and Associated Programs of the Society for Immunotherapy of Cancer," Retrieved from the Internet: URL: http://pulsebiosciences.com/assets/Pulse%20AIR%20poster.pdf, retrieved on Mar. 13, 2018.
Anand et al., "Nano-Pulse Electro-Signaling treatment of murine tumors significantly reduces the percentage of regulatory T cells in the treated tumor," Journal for Immunotherapy of Cancer: 31 st Annual Mffting and Associated Programs of the Society for Immunotherapy of Cancer (SITC 2016), Part Two, National Harbor, MD, USA Nov. 16, 2016, p. 214.
Beebe, S. J., "Hepatocellular carcinoma ablation and possible immunity in the age of nanosecond pulsed electric fields," Journal of Hepatocellular Carcioma, May 2015, No. 2, pp. 49-55.
McDaniel et al., "Nanosecond pulsed electric field treatment of tumor cell lines triggers immunogenic cell death (ICD)," Nov. 11, 2016, Poster presentation at the 31st Annual Meeting and Associated Programs of the Society for Immunotherapy of Cancer (SITC 2016), National Harbor, MD, USA; Retrieved from the Internet: URL: http://pulsebiosciences.com/assets/Pulse%20ICD%20poster.pdf, retrieved on Mar. 13, 2018.
McDaniel et al., "P329 Nanosecond pulsed electric field treatment of tumor cell lines triggers immunogenic cell death (ICD)," Journal for ImmunoTherapy of Cancer: 31st Annual Meeting and Associated Programs of the Society for Immunotherapy of Cancer (SITC 2016): part two: National Harbor, MD, USA, Nov. 16, 2016, p. 175.
PCT/US2017/057698, "International Search Report" dated Feb. 27, 2018, 3 pages.
PCT/US2017/064685, "International Search Report" dated Mar. 22, 2018, 5 pages.
PCT/US2018/019213, "International Search Report" dated May 22, 2018, 4 pages.
PCT/US2017/060654, "International Search Report and Written Opinion," dated Feb. 27, 2018, 18 pages.
Garon et al., "In Vitro and In Vivo Evaluation and a Case Report of Intense Nanosecond Pulsed Electric Field as a Local Therapy for Human Malignancies", Int. J. Cancer, vol. 121, 2007, pp. 675-682.
Gundersen et al., "Nanosecond Pulse Generator Using a Fast Recovery Diode", IEEE 26.sup.th Power Modulator Conference, 2004, pp. 603-606.

International Application No. PCT/US2015/63025, International Search Report and Written Opinion dated Apr. 21, 2016, 9 pages.
Nader Yatim et al., "RIPK1 and NF-1<B signaling in dying cells determines cross-priming of cos• T cells," Science, Oct. 2015, vol. 350, Issue 6258, pp. 328-335, sciencemag.org.
PCT/US2017/052340, "International Search Report and Written Opinion", dated Jan. 8, 2018, 12 pages.
Tang et al., "Diode Opening Switch Based Nanosecond High Voltage Pulse Generators for Biological and Medical Applications", IEEE Transactions on Dielectrics and Electrical Insulation, vol. 14, No. 4, 2007, pp. 878-883.
Wang et al., "Solid-State High Voltage Nanosecond Pulse Generator," IEEE Pulsed Power Conference, 2005, pp. 1199-1202.
PCT/US2017//032744, "International Search Report and Written Opinion," dated Jul. 21, 2017, 11 pages.
PCT/US2017/015884, "International Search Report and Written Opinion" dated Apr. 21, 2017, 12 pages.
International Application No. PCT/US2017/015881, Invitation to Pay Additional Fees And, Where Applicable, Protest Fee, mailed Mar. 15, 2017, 2 pages.
R. J. Baker et al., "Stacking Power MOSFETs for use in High Speed Instrumentation," Rev. Sci. Instrum. 63 (12), Dec. 1992. p 5799-5801, vol. 63, No. 12, American Institute of Pt1ysics.
H. Kirbie et al., "An All Solid State Pulse Power Source for High PRF Induction Acceslerators," IEEE 1998, p. 6-11.
K. Okamura et al., "Development of the High Repetitive Impulse Voltage Generator Using Semiconductor Switches," IEEE 1999, p. 807-810.
A. Krasnykh et al., "A Solid State Maix Type Modulator for Driving a TWT" Conference Record of the 24th, International Power Modulator Sypolsium 2000, p. 209-211.
R.J. Richter-Sand et al., "Marx-Stacked IGBT Modulators for High Voltage, High Power Applications," IEEE 2002, p. 390-393.
Marcel P.J. Gaudreau et al., "Solid-State Pulsed Power Systems for the Next linear Collider," IEEE 2002. p. 298-301.
E.G. Cook et al., "Design and Testing of a Fast, 50 kV Solid-State Kicker Pulser," IEEE 2002. p. 106-109.
Jeffrey A. Casey et al., "Solid-State Marx Bank Modulator for the Next Generation Linear Collider," Conference Record of the 26'h International Power Modulator Symposium and 2004 High Voltage Workshop {PMC), San Francisco, California. May 23-26, 2004, IEEE 2004, p. 257-260.
W. Jiang et al., "Marx Generator Using Power Mosfets," IEEE 2009, p. 408-410.
Chenguo Yao et al., "FPGA-Controlled All-Solid-State Nanosecond Pulse Generator for Biological Applications," IEEE Transactions on Plasma Science, vol. 40, No. 10, Oct. 2012, p. 2366-2372.
Martin Sack et al. "Design Considerations for a Fast Stacked-MOSFET Switch," IEEE Transactions on Plasma Science, vol. 41, No. 10, Oct. 20, 2013, p. 2630-2636.
Harshada C. Bhosale et al., "Design and Simulation of 50 kV, 50 A Solid State Marx Generator," International Conference on Magnetics, Machines & Drives (AICERA—2014 iCMMD), IEEE 2014, p. 1-5.
L. M. Redondo et al., "Solid-State Marx Generator Design with an Energy Recovery Reset Circuit for Output Transformer Association" 5 pages.
W. J. Carey et al., "Marx Generator Design and Performance," Applied Physical Electronics, L.C., 4 pages.
PCT/US2017/015881, "International Search Report and Written Opinion" dated May 25, 2017, 13 pages.
Engish Translation of the Japanese Office Action dated Jul. 23, 2019, in Japanese Application No. 2018-561184, 3 pages.

* cited by examiner

HIGH-VOLTAGE ANALOG CIRCUIT PULSER AND PULSE GENERATOR DISCHARGE CIRCUIT

CROSS-REFERENCES TO RELATED APPLICATIONS

This application is a divisional of and claims the benefit of co-pending U.S. application Ser. No. 15/347,729, filed Nov. 9, 2016, titled "HIGH-VOLTAGE ANALOG CIRCUIT PULSER AND PULSE GENERATOR DISCHARGE CIRCUIT," which is a continuation-in-part of U.S. application Ser. No. 15/148,344, filed May 6, 2016, titled "HIGH-VOLTAGE ANALOG CIRCUIT PULSER WITH FEEDBACK CONTROL," which claims the benefit of U.S. provisional application No. 62/301,477 filed Feb. 29, 2016, titled "HIGH-VOLTAGE ANALOG CIRCUIT PULSER," each of which are incorporated herein by reference in their entirety for all purposes.

BACKGROUND

1. Field of the Invention

The present application generally relates to electrical pulse techniques including circuits and systems for generating electric pulses, including the use of an energy-accumulating element discharged through a load by a relatively low voltage transistor and for controlling the discharge. Specifically, the pulse techniques are used for generating variable duration nanosecond pulsed electric fields (nsPEF) for electrotherapy.

2. Description of the Related Art

Surgical excision of a tumor can result in an infection and leave a scar. Furthermore, if there are more tumors, every cancerous tumor should be identified and individually excised by a surgeon. This can be time consuming and expensive, not to mention uncomfortable for patients.

Cancerous tumors that are internal to a patient may be especially difficult to remove, let alone detect and treat. Many patients' lives are turned upside down by the discovery of cancer in their bodies, sometimes which have formed relatively large tumors before being detected.

A "nanosecond pulsed electric field," sometimes abbreviated as nsPEF, includes an electric field with a sub-microsecond pulse width of, for example, between 0.1 nanoseconds (ns) and 1000 nanoseconds, or as otherwise known in the art. It is sometimes referred to as sub-microsecond pulsed electric field. NsPEFs often have high peak voltages, such as 10 kilovolts per centimeter (kV/cm), 20 kV/cm, to 500 kV/cm. Treatment of biological cells with nsPEF technology often uses a multitude of periodic pulses at a frequency ranging from 0.1 per second (Hz) to 10,000 Hz.

NsPEFs have been found to trigger apoptosis in cancerous tumors. Selective treatment of such tumors with nsPEFs can induce apoptosis within the tumor cells without substantially affecting normal cells in the surrounding tissue due to its non-thermal nature.

An example of nsPEF applied to biological cells is shown and described in U.S. Pat. No. 6,326,177 (to Schoenbach et al.), which is incorporated herein by reference in its entirety for all purposes.

The use of nsPEF for the treatment of tumors is a relatively new field. The nsPEF pulses are generated from a charged pulse generator, and there exists a need for a device with better control over pulse generator charge state for safe and effective studies and treatments of cancer in human subjects.

BRIEF SUMMARY

Generally, a nanosecond pulsed electrice field (nsPEF) generator is disclosed that incorporates one or more energy storage devices used to generate nsPEFs and a discharge circuit which can be selectively used to discharge the energy storage devices. For example, one or more capacitors may be used to store charge and used to generate nsPEFs to be applied to a patient or a test subject. In addition, the nsPEF generator may also have a discharge circuit, configured to selectively discharge the storage capacitors.

Selectively discharging the storage capacitors may be beneficial at least to reduce the risk of damage to the pulse generator posed by the stored energy of the energy storage devices, to reduce the risk of harm to nsPEF generator operators, patients and test subjects, and to provide increased control of pulse parameters.

One inventive aspect is a pulse generator discharge circuit. The circuit includes one or more discharge stages, each discharge stage including a plurality of control input terminals. The circuit also includes first and second discharge terminals, and a plurality of serially connected switches electrically connected between the first and second discharge terminals, where a conductive state of each of the switches is controlled by a control signal. The circuit also includes a plurality of inductive elements configured to generate the control signals for the serially connected switches, where each inductive element is configured to generate a control signal for one of the serially connected switches in response to one or more input signals at one or more of the control input terminals, and where each of the serially connected switches is configured to receive a control signal from a respective one of the inductive elements.

Another inventive aspect is a nanosecond pulsed electric field (nsPEF) generator system, including a pair of electrodes configured to deliver a nsPEF pulse to a patient, and a Marx generator apparatus. The Marx generator apparatus includes a power source, and a plurality of pulse generator stages. Each pulse generator stage includes a capacitive element configured to be charged by the power source and configured to be discharged through the electrodes. The generator system also includes a discharge circuit, configured to selectively discharge the capacitive elements of the stages.

Another inventive aspect is a method of operating a nanosecond pulsed electric field (nsPEF) generator system. The method includes delivering a first nsPEF pulse to a patient with a pair of electrodes of the system, the first nsPEF pulse having a first voltage, discharging the system to a different charge voltage with a discharge circuit, and delivering a second nsPEF pulse to the patient with the pair of electrodes.

Another inventive aspect is a method of operating a nanosecond pulsed electric field (nsPEF) generator system. The method includes charging the system to a charge voltage with current from one or more power supplies, determining that an nsPEF pulse is to be delivered to a patient, delivering an nsPEF pulse to the patient with a pair of electrodes of the system, and determining that no further nsPEF pulses are to be delivered to the patient. The method also includes, in response to determining that no further nsPEF pulses are to be delivered to the patient, discharging the system to a different charge voltage with a discharge circuit.

DETAILED DESCRIPTION

It has been shown that nsPEF treatments can be used to cause cancerous tumor cells to undergo apoptosis, a programmed cell death. Tests have shown that tumors can shrink to nonexistence after treatment. No drugs may be necessary. It has also been shown that the subject's immune system may be stimulated to attack all similar tumor cells, including those of tumors that are not within the nsPEF-treated tumor.

A "tumor" includes any neoplasm or abnormal, unwanted growth of tissue on or within a subject, or as otherwise known in the art. A tumor can include a collection of one or more cells exhibiting abnormal growth. There are many types of tumors. A malignant tumor is cancerous, a pre-malignant tumor is precancerous, and a benign tumor is noncancerous. Examples of tumors include a benign prostatic hyperplasia (BPH), uterine fibroid, pancreatic carcinoma, liver carcinoma, kidney carcinoma, colon carcinoma, pre-basal cell carcinoma, and tissue associated with Barrett's esophagus.

A "disease" includes any abnormal condition in or on a subject that is associated with abnormal, uncontrolled growths of tissue, including those that are cancerous, precancerous, and benign, or other diseases as known in the art.

"Apoptosis" of a tumor or cell includes an orderly, programmed cell death, or as otherwise known in the art.

"Immunogenic apoptosis" of a tumor or cell includes a programmed cell death that is followed by an immune system response, or as otherwise known in the art. The immune system response is thought to be engaged when the apoptotic cells express calreticulin or another antigen on their surfaces, which stimulates dendritic cells to engulf, consume, or otherwise commit phagocytosis of the targeted cells leading to the consequent activation of a specific T cell response against the target tumor or cell.

Pulse lengths of between 10 and 900 nanoseconds for nsPEF have been particularly studied to be effective in stimulating an immune response. Pulse lengths of about 100 nanoseconds are of particular interest in that they are long enough to carry sufficient energy to be effective at low pulse numbers but short enough to be effective in the manner desired.

A time of "about" a certain number of nanoseconds includes times within a tolerance of ±1%, 2%, 3%, 4%, 5%, 7.5%, 10%, 15%, 20%, 25% or other percentages, or fixed tolerances, such as ±0.1, ±0.2, ±0.3, ±0.4, ±0.5, ±0.7, ±1.0, ±2.0, ±3.0, ±4.0±5.0, ±7.0, ±10, ±15, ±20, ±25, ±30, ±40, ±50, ±75 ns, or other tolerances as acceptable in the art in conformance with the effectivity of the time period.

Immune system biomarkers can be measured before and/or after nsPEF treatment in order to confirm that the immune response has been triggered in a patient. Further, nsPEF treatment can be paired with a CD47-blocking antibody treatment to better train CD8+T cells (i.e., cytotoxic T cells) for attacking the cancer.

Figure 1:
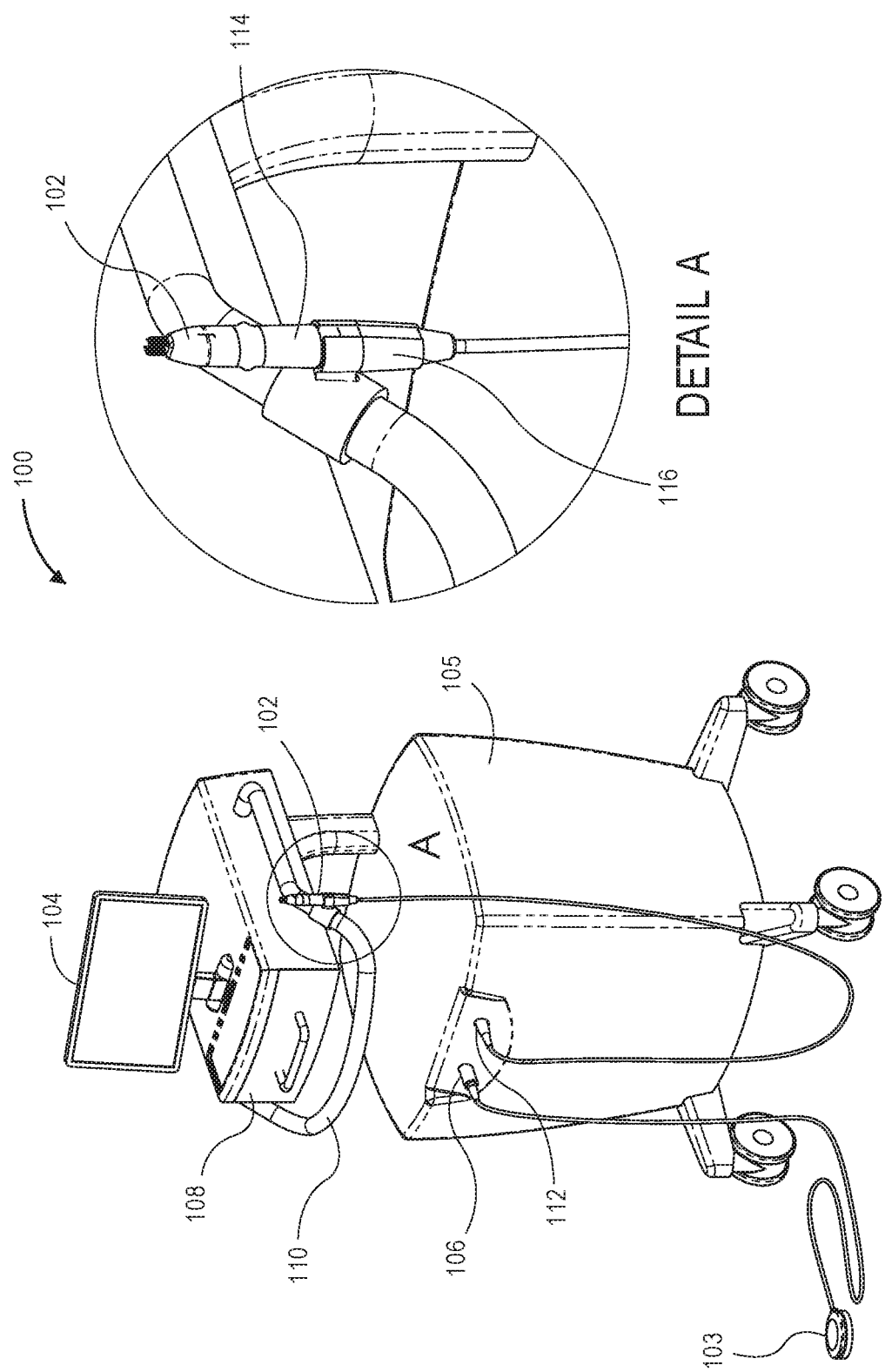
FIG. 1 illustrates a nanosecond pulse generator apparatus in accordance with an embodiment.

FIG. 1 illustrates a nanosecond pulse generator system in accordance with an embodiment. NsPEF system 100 includes electrode 102, footswitch 103, and interface 104. Footswitch 103 is connected to housing 105 and the electronic components therein through connector 106. Electrode 102 is connected to housing 105 and the electronic components therein through high voltage connector 112. NsPEF system 100 also includes a handle 110 and storage drawer 108. As shown in DETAIL A portion of FIG. 1, nsPEF system 100 also includes holster 116, which is configured to hold electrode 102 at its handle portion 114.

A human operator inputs a number of pulses, amplitude, pulse duration, and frequency information, for example, into a numeric keypad or a touch screen of interface 104. In some embodiments, the pulse width can be varied. A microcontroller sends signals to pulse control elements within nsPEF system 100. In some embodiments, fiber optic cables allow control signaling while also electrically isolating the contents of the metal cabinet with nsPEF generation system 100, the high voltage circuit, from the outside. In order to further isolate the system, system 100 may be battery powered instead of from a wall outlet.

Figure 2:
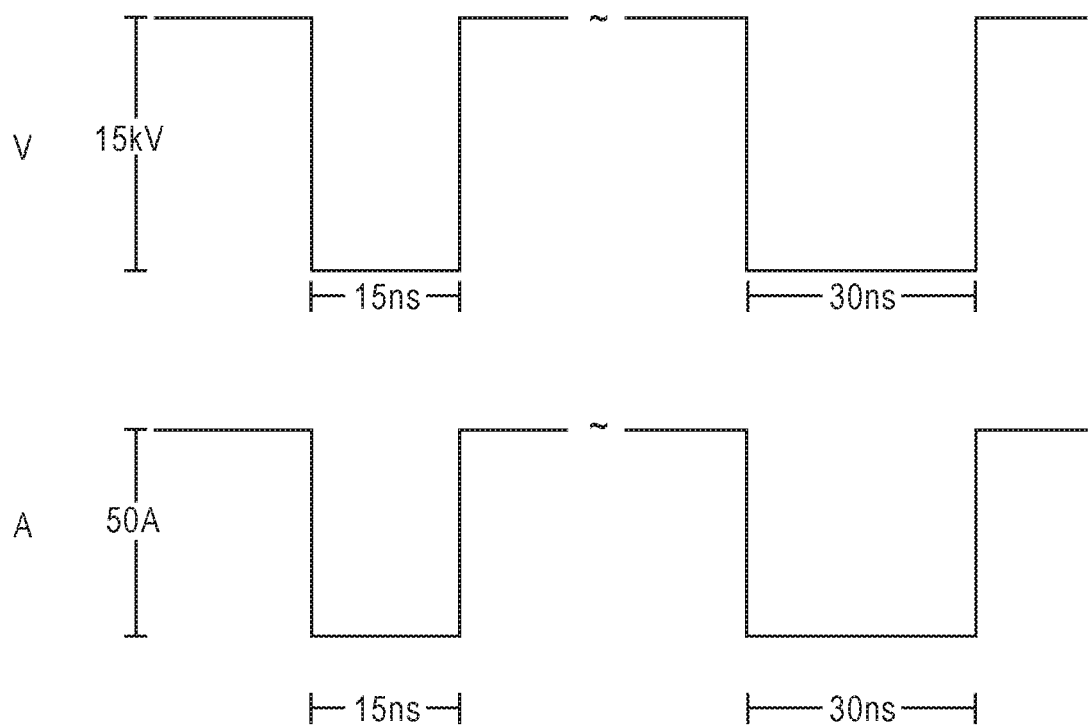
FIG. 2 illustrates a pulse profile for both voltage and current in accordance with an embodiment.

FIG. 2 illustrates a pulse profile for both voltage and current in accordance with an embodiment. Output from the nsPEF system 100 with voltage on the top of the figure and current on the bottom for a first and second pulses. The first pulse has an amplitude of about 15 kV, a current of about 50 A, and a duration of about 15 ns. The second pulse has an amplitude of about 15 kV, a current of about 50 A, and a duration of about 30 ns. If such a pulse had been delivered on suction electrodes having 4 mm between the plates, the pulse generator would have delivered a pulse of about 50 A and 37.5 kV/cm. Given a voltage, current depends heavily on the electrode type and tissue resistance.

While FIG. 2 illustrates a specific example, other pulse profiles may also be generated. For example, in some embodiments, rise and/or fall times for pulses may be less than 20 ns, about 20 ns, about 25 ns, about 30 ns, about 40 ns, about 50 ns, about 60 ns, about 75 ns, or greater than 75 ns. In some embodiments, the pulse voltage may be less than 5 kV, about 5 kV, about 10 kV, about 15 kV, about 20 kV, about 25 kV, about 30 kV, or greater than 30 kV. In some embodiments, the current may be less than 10 A, about 10 A, about 25 A, about 40 A, about 50 A, about 60 A, about 75 A, about 100 A, about 125 A, about 150 A, about 175 A, about 200 A, or more than 200 A. In some embodiments, the pulse duration may be less than 10 ns, about 10 ns, about 15 ns, about 20 ns, about 25 ns, about 30 ns, about 40 ns, about 50 ns, about 60 ns, about 75 ns, about 100 ns, about 125 ns, about 150 ns, about 175 ns, about 200 ns, about 300 ns, about 400 ns, about 500 ns, about 750 ns, about 1 µs, about 2 µs, about 3 µs, about 4 µs, about 5 µs, or greater than 5 µs.

Figure 3:
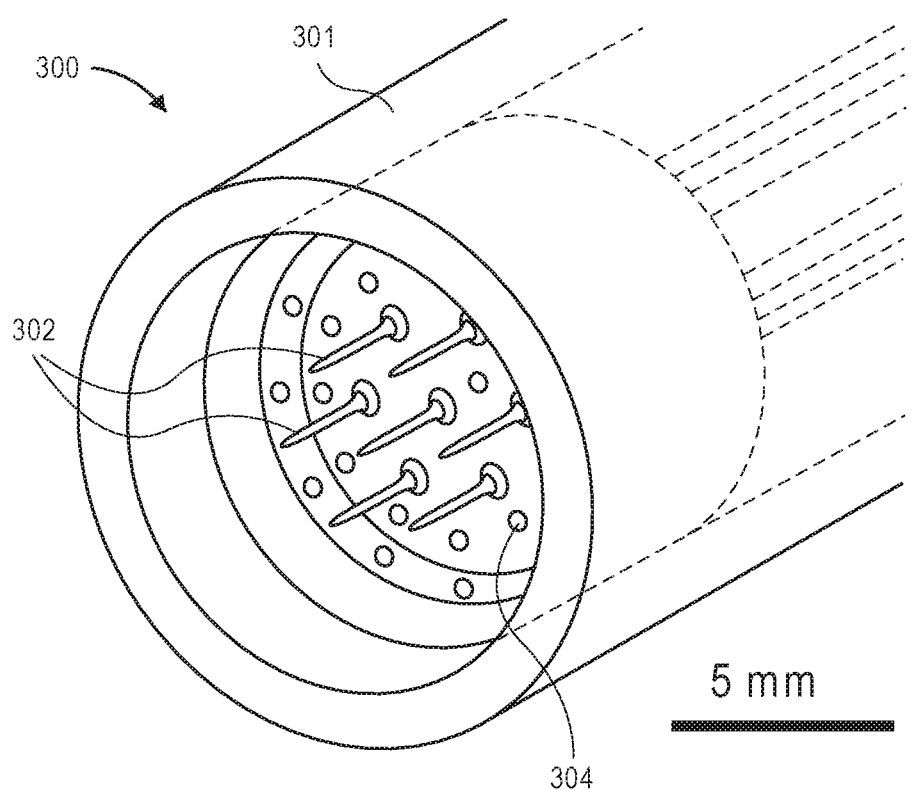
FIG. 3 illustrates a perspective view of a seven-needle electrode in accordance with an embodiment.

FIG. 3 illustrates a perspective view of a seven-needle suction electrode in accordance with an embodiment. In electrode 300, sheath 301 surrounds seven sharp electrodes 302 with a broad opening at a distal end. When the open end is placed against a tumor, air is evacuated from the resulting chamber through vacuum holes 304 to draw the entire tumor or a portion thereof into the chamber. The tumor is drawn so that one or more of the electrodes preferably penetrates the tumor. Sharp ends of the electrodes are configured to pierce the tumor. The center electrode may be at one polarity, and the outer six electrodes may be at the opposite polarity. Nanopulses electric fields can then be precisely applied to the tumor using nsPEF system 100 (see FIG. 1).

The electrodes can be opposed, one of each positive and negative pair of electrodes on one side of a tumor and the other electrode of the pair on an opposing side of the tumor. Opposing sides of a tumor can include areas outside or within a tumor, such as if a needle electrode pierces a portion of the tumor.

Figure 4:
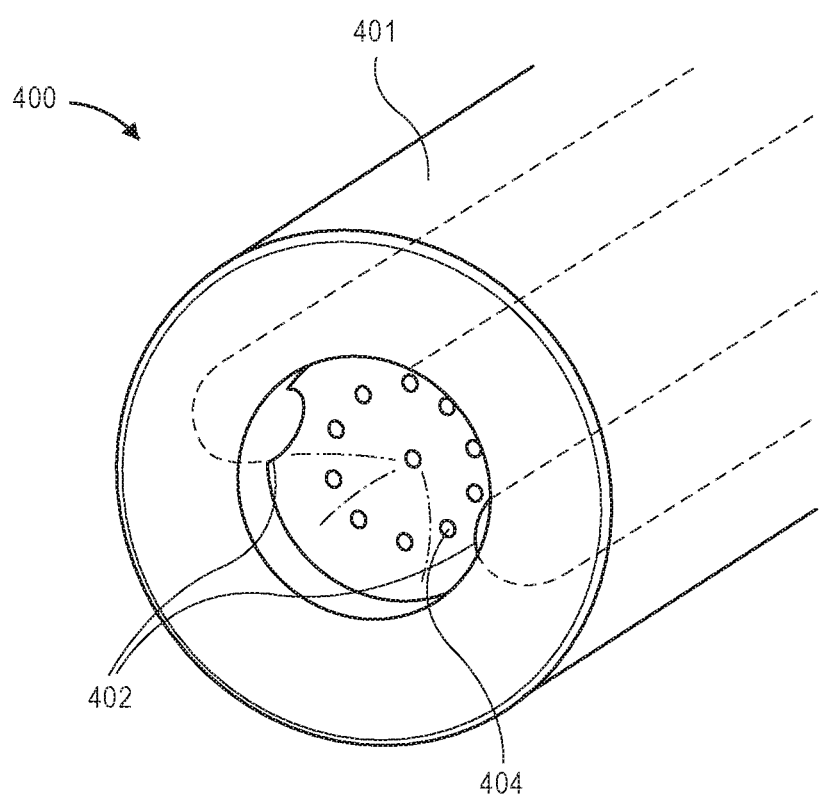
FIG. 4 illustrates a perspective view of a two-pole electrode in accordance with an embodiment.

FIG. 4 illustrates a two-pole suction electrode in accordance with an embodiment. In electrode device 400, sheath 401 surrounds two broad electrodes 402 on opposite sides of a chamber. When air is evacuated through vacuum holes 404 and a tumor is pulled within the chamber, the opposing electrodes apply nsPEF pulses to the tumor.

The nature of the electrode used mainly depends upon the shape of the tumor. Its physical size and stiffness can also be taken into account in selection of a particular electrode type.

U.S. Pat. No. 8,688,227 B2 (to Nuccitelli et al.) discloses other suction electrode-based medical instruments and systems for therapeutic electrotherapy, and it is hereby incorporated by reference.

If there are multiple tumors in a subject, a surgeon can select a single tumor to treat based on the tumor's compatibility with electrodes. For example, a tumor that is adjacent to a stomach wall may be more easily accessible than one adjacent a spine or the brain. Because a nsPEF pulse is preferably applied so that the electric field transits through as much tumor mass as possible while minimizing the mass of non-tumor cells that are affected, a clear path to two opposed 'poles' of a tumor may also be a selection criterion.

For tumors on or just underneath the skin of subject, needle electrodes can be used percutaneously. For locations deeper within a subject, a retractable electrode can fit into a gastroscope, bronchoscope, colonoscope, or other endoscope or laparoscope. For example, a tumor in a patient's colon can be accessed and treated using an electrode within a colonoscope. For tumors within the body, electrodes can be used in open surgery, laparoscopic surgery, or through other minimally invasive surgical approaches.

Barrett's esophagus, in which portions of tissue lining a patient's esophagus are damaged, may be treated using an electrode placed on an inflatable balloon.

Embodiments of nanosecond pulsed power generators produce electric pulses in the range of single nanoseconds to single microseconds. The pulses are created by rapid release of energy stored in, for example, a capacitive or inductive energy reservoir to a load in a period that is generally much shorter than the charging time of the energy reservoir.

Conventional capacitive-type pulsed generators include pulse forming networks, which provide fixed pulse duration and impedance. With prior knowledge of a load's resistance, a pulse forming network with impedance that matches the load can be used. But for broader applications, especially when the load resistance is unknown, it is desirable to have a pulse generator with a flexibility of impedance matching and variation of pulse duration. Such flexibility can be implemented by switching a capacitor with a controllable switch. In this case, the capacitor can be regarded as a "voltage source" and can adapt to various load resistance. The switched pulse amplitude can then have the same voltage as the voltage of the capacitor. The pulse width is accordingly determined by the switch "on" time.

The selection of switches in nanosecond pulse generators is limited because of the high voltages, high currents, and fast switching times involved.

Spark gap switches, typically used in pulsed power technology, are capable of switching high voltages and conducting high currents. But they can only be turned on, and stopping the current flow in the middle of conduction is impossible. Besides spark gaps, other types of high voltage, high power switches are available, such as: magnetic switches, vacuum switches (Thyratrons for example), and certain high-voltage semiconductor switches.

Magnetic switches, relying on the saturation of magnetic core, change from high impedance to low impedance in the circuit. They can be turned on above a certain current threshold but will not be turned off until all the current is depleted by the load.

Vacuum switches are a good option for high voltage and high repletion rate operation, but similar to magnetic switches, they also can be only turned on, but cannot be turned off at a predetermined time.

Some types of high-voltage semi-conductor switches may also be considered. Thyristors and insulated gate bipolar transistors (IGBTs) may, in some embodiments be used. However, the turn-on times of Thyristors and IGBTs limit their usefulness.

Metal-oxide-semiconductor field-effect transistors (MOSFETs) have insufficient maximum drain to source voltage ratings (e.g. <1 kV) and insufficient maximum drain to source current ratings (e.g. <50 A) to be used in conventional pulse generator architectures to produce the voltage and current necessary for the applications discussed herein. If they were used, a large number of stages would be needed in order to produce high-amplitude output voltages. However, in conventional Marx generator architectures with a large number of stages, the Marx generator goes into an underdamped mode instead of a critically damped mode, resulting in loss in overshoot. As a result, the overall voltage efficiency decreases. For example, a voltage efficiency of a Marx generator may be 80% at 5 stages but decrease to 50% at 20 stages.

Furthermore, as the number of stages is increased, the impedance of the Marx generator also increases. This reduces the total energy deliverable to the load. This is particularly unfavorable for driving low impedance loads and long pulses.

In addition, the charging losses in the charging resistors also increases with the increased number of stages. As a result, such Marx generators are unsuitable for high repetition rate operation.

Therefore, in order to produce high voltage pulses, simply increasing the number of stages will cause a series of problems, including low efficiency, high impedance, etc. Because there is a tradeoff between the number of the stages and the actual output voltage, using conventional Marx generators cannot produce high voltage pulses which are sufficient for the applications discussed herein.

Some embodiments of this disclosure include a tunable, high voltage, nanosecond pulse generator. The switches may be power MOSFETs, which may, for example, be rated for a voltage of 1 kV and current of up to 30 A. In some embodiments, the switches power MOSFETs rated for a voltage of 1 kV and current of up to continuous 90 A and more than 200 A peak. Voltage is scaled up by a Marx-switch stack hybrid circuit. In each Marx generator stage, a particularly configured stack of MOSFETs is used. As a result, the charging voltage for each stage is greater than the rated maximum for a single switch.

A technical advantage of the configuration is that the overall output voltage can be increased with just a few stages (e.g. <=5). As a result, the problems discussed above with Marx generators having a large number of stages are avoided and high efficiency, low impedance, and large variability in the pulse duration can be achieved.

Such an architecture also allows much easier control as only one trigger circuit may be needed for each stage. One additional benefit is that the pulse generator has low impedance, so it will be able to drive various loads with high current and extended pulse duration. The scaling up of the current is implemented by combining multiple Marx-switch stack circuits in parallel. The pulse duration is controlled by the closing and opening of the switch stack switches.

Figure 5:
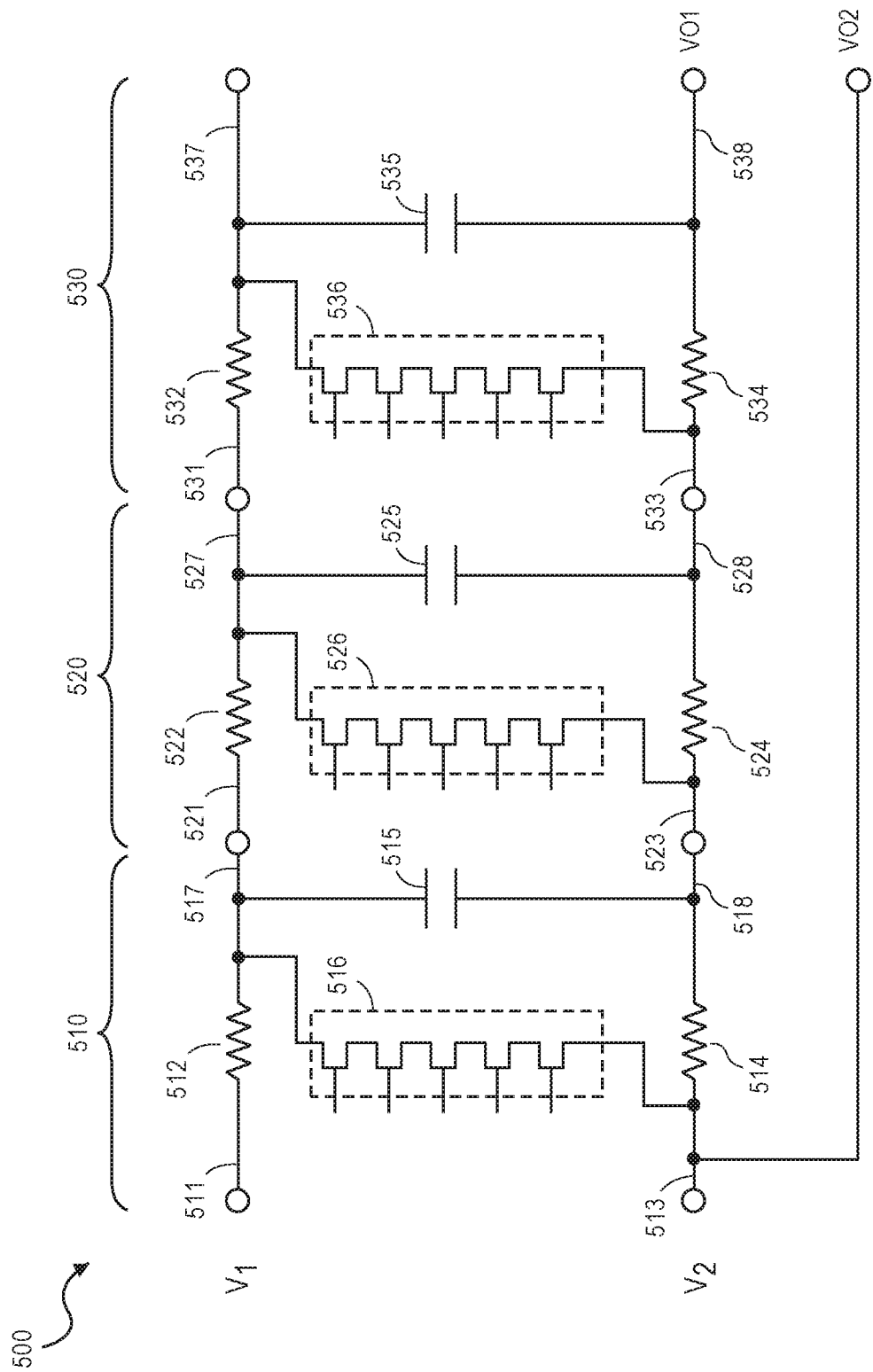
FIG. 5 is an electrical schematic of a pulse generator in accordance with an embodiment.

FIG. 5 illustrates a pulse generator circuit 500 which may be used inside nsPEF system 100 of FIG. 1. Pulse generator circuit 500 illustrates a panel comprising a Marx generator switched by three switch stacks. The nsPEF system can have a single pulse generator circuit panel. In some embodiments, a nsPEF system includes multiple panels in parallel.

Circuit 500 includes three stages—510, 520, and 530. In some embodiments, another number of stages is used. For example, in some embodiments, 2, 4, 5, 6, 7, 8, 9, or 10 stages are used. Stage 510 includes resistors 512 and 514, capacitor 515, and switch stack 516. Likewise, stage 520 includes resistors 522 and 524, capacitor 525, and switch stack 526, and stage 530 includes resistors 532 and 534, capacitor 535, and switch stack 536. Each of these elements have structure and functionality which is similar to the corresponding elements of stage 510.

Stage 510 has first and second input voltage input terminals 511 and 513 and first and second voltage output terminals 517 and 518. Stage 520 has first and second input voltage input terminals 521 and 523, and first and second voltage output terminals 527 and 528. Stage 530 has first and second input voltage input terminals 531 and 533, and first and second voltage output terminals 537 and 538.

The first and second voltage input terminals 511 and 513 of stage 510 are respectively connected to first and second power supply input terminals V1 and V2. The first and second voltage output terminals 517 and 518 of stage 510 are respectively connected to the first and second voltage input terminals 521 and 523 of stage 520. The first and second voltage output terminals 527 and 528 of stage 520 are respectively connected to the first and second voltage input terminals 531 and 533 of stage 530. The second voltage output terminal 538 of stage 530 and second voltage input terminal 513 of stage 510 are respectively connected to first and second power output terminals VO1 and VO2.

Pulse generator circuit 500 operates in a charge mode, and in a discharge mode. During the charge mode, described below with reference to FIG. 6A in more detail, capacitors 515, 525, and 535 are charged to a charge voltage by current received from the first and second power supply input terminals V1 and V2. During the discharge mode, described below with reference to FIG. 6B in more detail, capacitors 515, 525, and 535 are discharged to provide a current to a load (not shown) connected across first and second power output terminals VO1 and VO2.

Figure 6A:
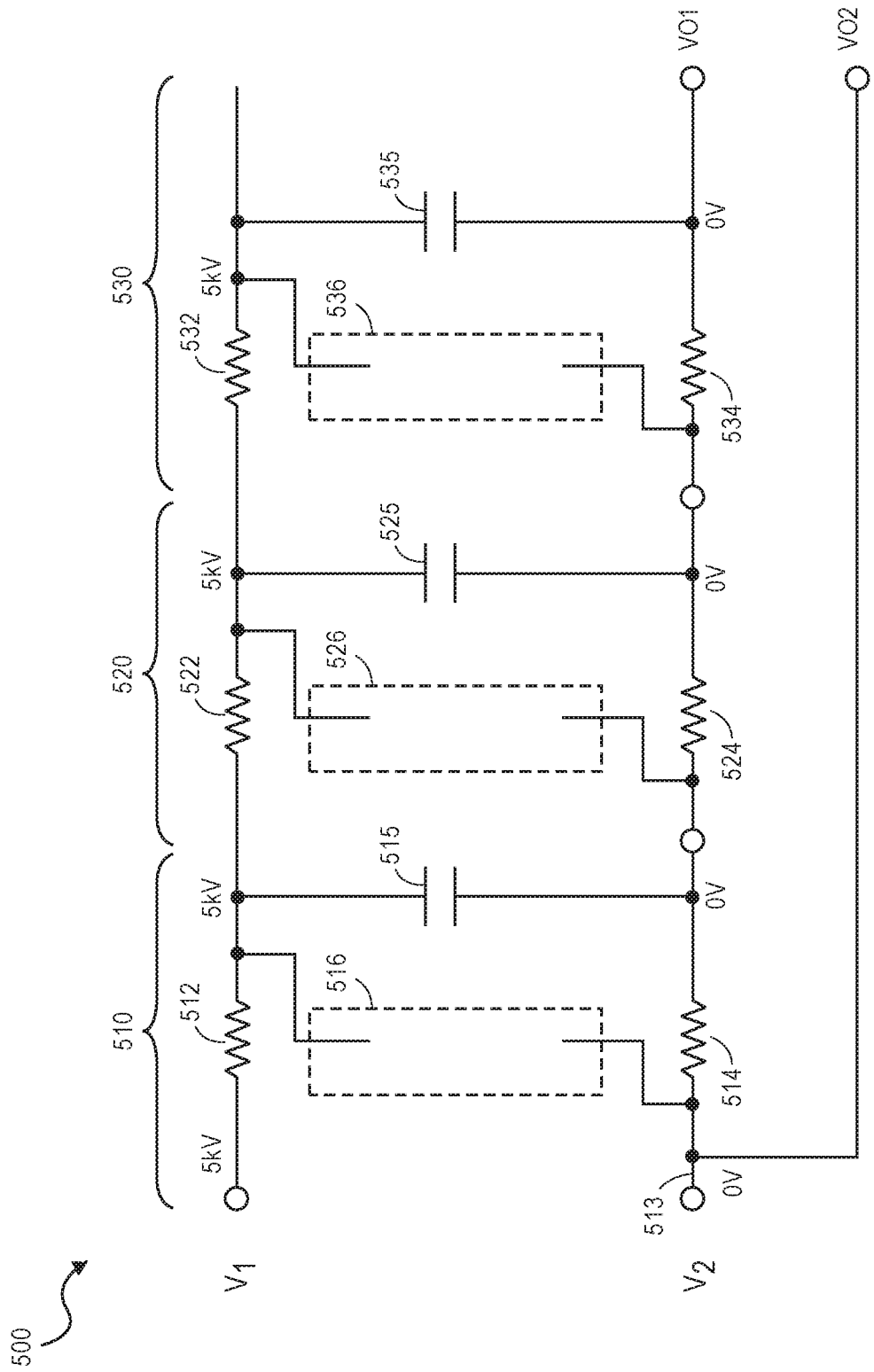
FIG. 6A is a schematic illustrating the pulse generator shown in FIG. 5 during charge mode.

FIG. 6A illustrates pulse generator circuit 500 during charge mode. First and second input voltages are respectively applied to first and second power supply input terminals V1 and V2 while each of switch stacks 516, 526, and 536 are nonconductive or open, and while first and second power output terminals may be disconnected from the load (not shown). Because each of switch stacks 516, 526, and 536 are open, substantially no current flows therethrough, and they are represented as open circuits in FIG. 6A. During the charge mode, each of capacitors 515, 525, and 535 are charged to a charge voltage by current flowing through resistors 512, 522, 532, 534, 524, and 514 to or toward a voltage equal to the difference between the first and second input voltages.

Each of the switches of switch stacks 516, 526, and 536 has a breakdown voltage rating which should not be exceeded. However, because the switches are serially connected, the capacitors 515, 525, and 535 may be charged to a voltage significantly greater than the breakdown voltage of the individual switches. For example, the breakdown voltage of the switches may be 1 kV, and the capacitors 515, 525, and 535 may be charged to a voltage of 5 kV, when 5 or more switches are used in each switch stack.

For example, the first and second input voltages may respectively be 5 kV and 0V. In such an example, each of the capacitors 515, 525, and 535 is charged to or toward a voltage equal to 5 kV. In some embodiments, the difference between the first and second input voltages is limited to be less than 10 kV.

Figure 6B:
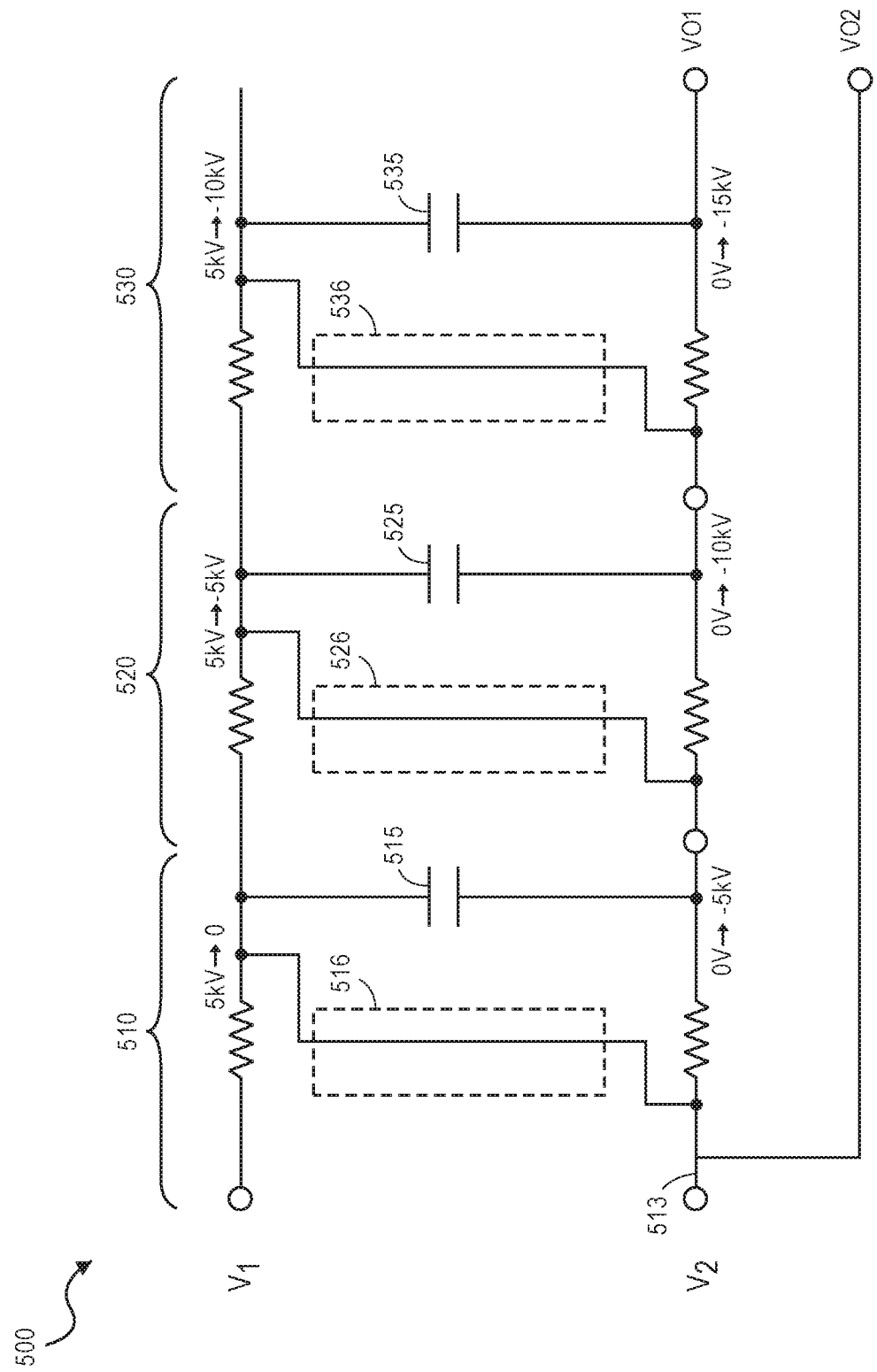
FIG. 6B is a schematic illustrating the pulse generator shown in FIG. 5 during discharge mode.

FIG. 6B illustrates pulse generator circuit 500 during discharge mode. First power supply input terminal V1 may be disconnected from the first input voltage. In some embodiments, first power supply input terminal V1 remains connected to the first input voltage. Second power supply input terminal V2 remains connected to the second input voltage. In addition, each of switch stacks 516, 526, and 536 are conductive or closed. Because each of switch stacks 516, 526, and 536 are closed, current flows therethrough, and they are represented as conductive wires in FIG. 6B. As a result, a low impedance electrical path from power supply input terminal V2 to power output terminal VO1 is formed by switch stack 516, capacitor 515, switch stack 526, capacitor 525, switch stack 536, and capacitor 535. Consequently, the difference between the voltages at the power output terminals VO1 and VO2 is equal to the number of stages (in this example, 3) times the difference between the first and second input voltages.

Where the first and second input voltages are respectively 5 kV and 0V, a voltage difference of 15 kV is developed across the power output terminals VO1 and VO2.

Figure 7:
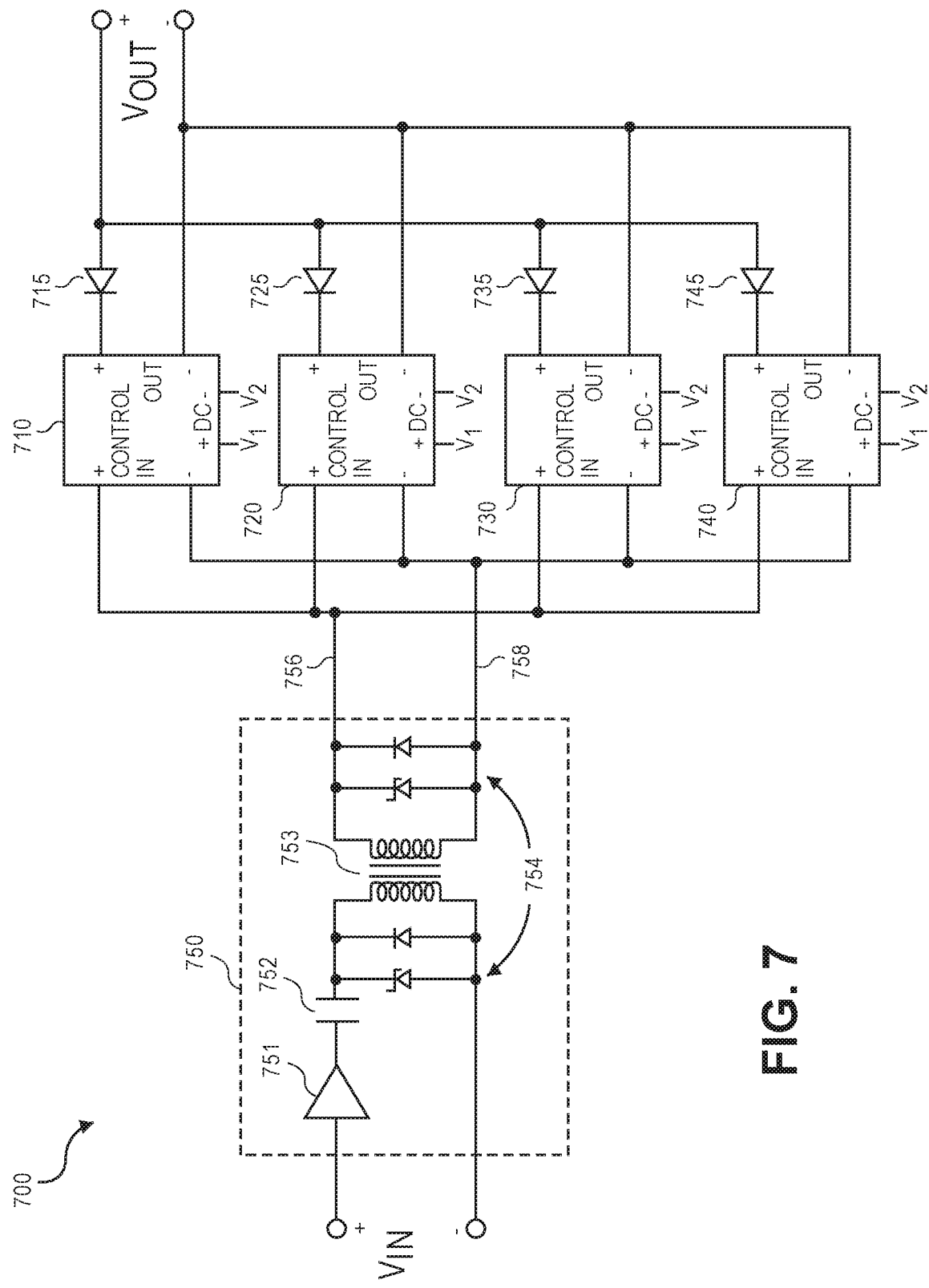
FIG. 7 is an electrical schematic of an assembly of pulse generator circuits.

FIG. 7 illustrates an alternative pulse generator circuit 700 which may be used inside nsPEF system 100 of FIG. 1. This pulse generator includes panels in parallel. The number of panels can be adjusted to allow the system to generate different amounts of current and power.

Pulse generator circuit 700 receives input pulses across input port Vin, and generates output pulses across output port Vout in response to the received input pulses.

Pulse generator circuit 700 includes multiple panels or pulse generator circuits 710, 720, 730, and 740. Pulse generator circuit 700 also includes driver 750. In this embodiment, four pulse generator circuits are used. In alternative embodiments, fewer or more pulse generator circuits are used. For example, in some embodiments, 2, 3, 5, 6, 7, 8, 9, 10 or another number of pulse generator circuits are used.

Each of the pulse generator circuits 710, 720, 730, and 740 may have characteristics similar to other pulse generator circuits discussed herein. For example, each the pulse generator circuits 710, 720, 730, and 740 may have characteristics similar to pulse generator circuit 500 discussed above with reference to FIGS. 5, 6A, and 6B.

Each of pulse generator circuits 710, 720, 730, and 740 has positive and negative DC input terminals, positive and negative control input terminals, and positive and negative output terminals, and is configured to generate output voltage pulses across the positive and negative output terminals in response to driving signal pulses applied across the positive and negative control input terminals. The output voltage pulses are also based on power voltages received across positive and negative DC power input terminals.

The driving signal pulses are generated across conductors 756 and 758 by driver 750, which includes amplifier circuit 751, capacitor 752, and transformer 753. In some embodiments, driver 750 also includes clamp circuits 754.

Driver 750 receives an input signal pulse at input port Vin and generates a driving signal pulse across conductors 756 and 758 in response to the input signal pulse Amplifier circuit 751 receives the input signal pulse and drives transformer 753 through capacitor 752, which blocks low frequency and DC signals. In response to being driven by amplifier circuit 751, transformer 753 generates an output voltage pulse across conductors 756 and 758, such that the duration of the output voltage pulse is equal to or substantially equal (e.g. within 10% or 1%) to the duration of the input signal pulse at input port Vin.

In some embodiments, clamp circuits 754 are included at least to dampen potential signals, which may otherwise be caused by resonance. Clamp circuits 754 include parallel diodes, which provide a short-circuit path for any current reversal, and also clamp the maximum voltage across the components connected to the clamp circuits 754.

In some embodiments, transformer 753 has a 1:1 turns ratio. In alternative embodiments, a different turns ratio is used.

Each of pulse generator circuits 710, 720, 730, and 740 receives the voltage pulses from driver 750 across the positive and negative control input terminals and generates corresponding voltage pulses across the positive and negative output terminals in response to the received voltage pulses from driver 750. The voltage pulses generated across the positive and negative output terminals have durations which are equal to or substantially equal (e.g. within 10% or 1%) to the durations of the voltage pulses received from driver 750.

In this embodiment, the negative output terminals of pulse generator circuits 710, 720, 730, and 740 are directly connected to the negative Vout terminal of the output port Vout of pulse generator circuit 700. In addition, in this embodiment, the positive output terminals of pulse generator circuits 710, 720, 730, and 740 are respectively connected to the positive Vout terminal of the output port Vout of pulse generator circuit 700 through diodes 715, 725, 735, and 745. Diodes 715, 725, 735, and 745 decouple pulse generator circuits 710, 720, 730, and 740 from one another. As a consequence, interference and the associated pulse distortion that would otherwise occur is substantially eliminated. For example, diodes 715, 725, 735, and 745 prevent current from one of pulse generator circuits 710, 720, 730, and 740 to another of pulse generator circuits 710, 720, 730, and 740 if the switching is not perfectly synchronous. Diodes 715, 725, 735, and 745 also prevent current from flowing from the pulse generator circuits 710, 720, 730, and 740 while they are charging.

In this embodiment, diodes 715, 725, 735, and 745 each include a single diode. In alternative embodiments, diodes 715, 725, 735, and 745 each include multiple diodes connected serially based at least upon voltage ratings of the serially connected diodes.

In this embodiment, diodes 715, 725, 735, and 745 are connected so as to conduct current from the positive terminal of output port Vout toward pulse generator circuits 710, 720, 730, and 740, as pulse generator circuits 710, 720, 730, and 740 in this embodiment are configured to generate negative pulses. In alternative embodiments, where pulse generator circuits are configured to generate positive pulses, diodes may be similarly connected so as to conduct current from the pulse generator circuits to the positive terminal of the output port.

Figure 8:
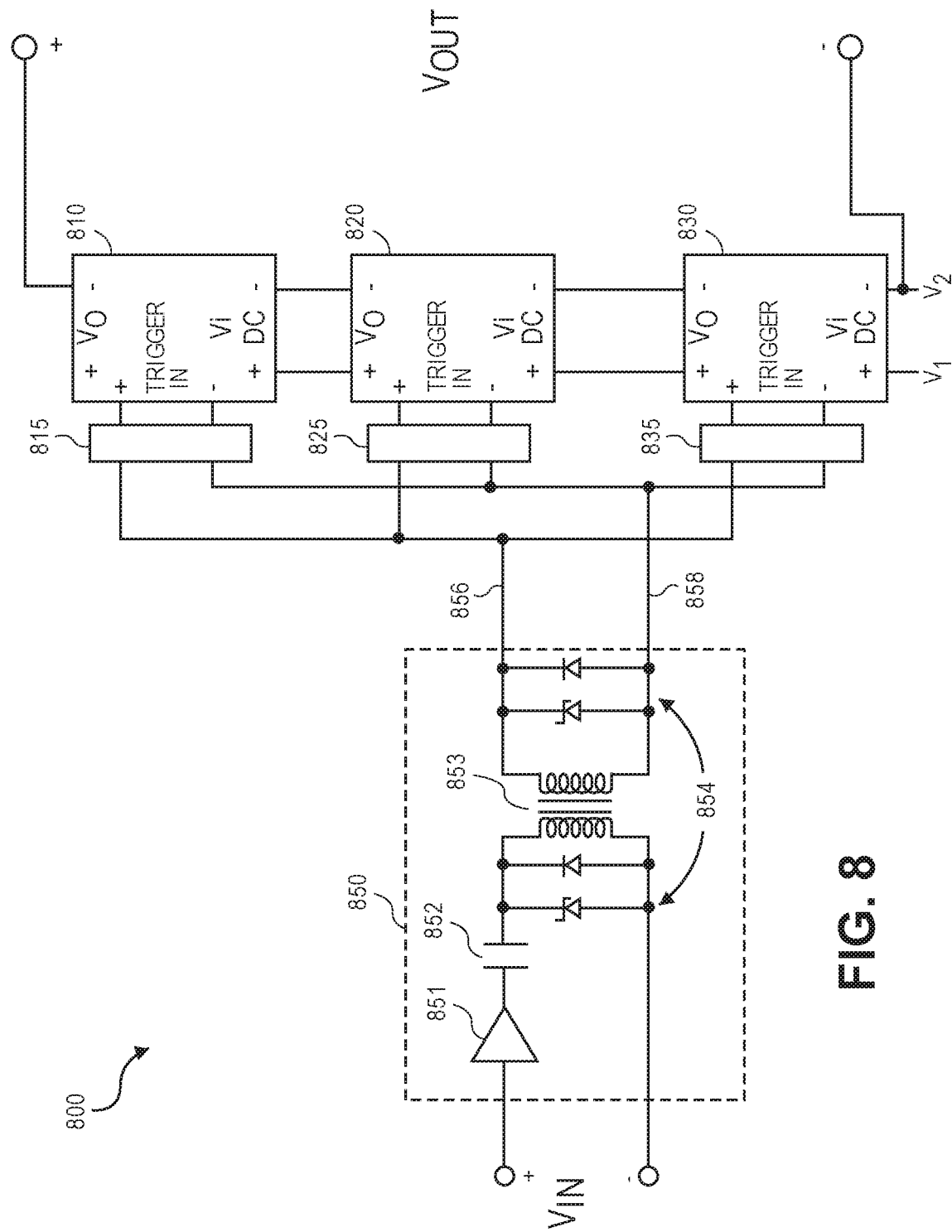
FIG. 8 is an electrical schematic of one of the pulse generator circuits shown in FIG. 7.

FIG. 8 illustrates a pulse generator circuit 800 which may be used for pulse generator circuits 710, 720, 730, and 740 of pulse generator circuit 700 of FIG. 7.

Pulse generator circuit 800 receives input pulses across input port Vin, and generates output pulses across output port Vout in response to the received input pulses.

Pulse generator circuit 800 includes multiple pulse generator stages 810, 820, and 830. In this embodiment, pulse generator circuit 800 also includes driver 850, and optional common mode chokes 815, 825, and 835.

Each of the pulse generator stages 810, 820, and 830 may have characteristics similar to other pulse generator stages discussed herein. For example, each the pulse generator stages 810, 820, and 830 may have characteristics similar to stages 510, 520, and 530 of pulse generator circuit 500 discussed above with reference to FIGS. 5, 6A, and 6B. In some embodiments, fewer or more pulse generator stages may be used.

Each of pulse generator stages 810, 820, and 830 has positive and negative trigger input terminals, power positive and negative DC input terminals, and positive and negative Vo output terminals, and is configured to generate output voltage pulses across the positive and negative Vo output terminals in response to driving signal pulses applied across the positive and negative trigger input terminals. The output voltage pulses are also based on power voltages V1 and V2 respectively received at power positive and negative DC input terminals.

In this embodiment, the negative Vi input terminal of pulse generator stage 830 is connected with the negative terminal of the output port Vout of pulse generator circuit 800. In addition, in this embodiment, the negative Vo output terminal of pulse generator stage 810 is connected with the positive terminal of the output port Vout of pulse generator circuit 800.

In addition, as shown, the positive Vo output terminal of pulse generator 830 is connected with the positive Vi input terminal of pulse generator 820, and the negative Vo output terminal of pulse generator 830 is connected with the negative Vi input terminal of pulse generator 820. Furthermore, the positive Vo output terminal of pulse generator 820 is connected with the positive Vi input terminal of pulse generator 810, and the negative Vo output terminal of pulse generator 820 is connected with the negative Vi input terminal of pulse generator 810.

The driving signal pulses for pulse generator stages 810, 820, and 830 are generated across conductors 856 and 858 by driver 850, which includes amplifier circuit 851, capacitor 852, and transformer 853. In some embodiments, driver 850 also includes clamp circuits 854.

Driver 850 receives an input signal pulse at input port Vin. Driver 850 generates a driving signal pulse across conductors 856 and 858 in response to the input signal pulse Amplifier circuit 851 receives the input signal pulse, and drives transformer 853 through capacitor 852, which reduces or blocks low frequency and DC signals. In response to being driven by amplifier circuit 851, transformer 853 generates an output voltage pulse across conductors 856 and 858, such that the duration of the output voltage pulse is equal to or substantially equal (e.g. within 10% or 1%) to the duration of the input signal pulse at input port Vin.

In some embodiments, clamp circuits 854 are included at least to dampen potential signals, which may otherwise be caused by resonance. Clamp circuits 854 include parallel diodes, which provide a short-circuit path for any current reversal, and also clamp the maximum voltage across the components connected to the clamp circuits 854.

In some embodiments, transformer 853 has a 1:1 turns ratio. In alternative embodiments, a different turns ratio is used.

Each of pulse generator stages 810, 820, and 830 receives the voltage pulses from driver 850 through a corresponding choke 815, 825, or 835, which blocks high frequency signals, for example, from coupling from the high voltage pulse generator stages 810, 820, and 830. The voltage pulses are received at the positive and negative trigger input terminals and the pulse generator stages 810, 820, and 830 each generate corresponding voltage pulses across the positive and negative Vo output terminals in response to the received voltage pulses from driver 850. The voltage pulses generated across the positive and negative Vo output terminals have durations which are equal to or substantially equal (e.g. within 10% or 1%) to the durations of the voltage pulses received from driver 850.

Figure 9:
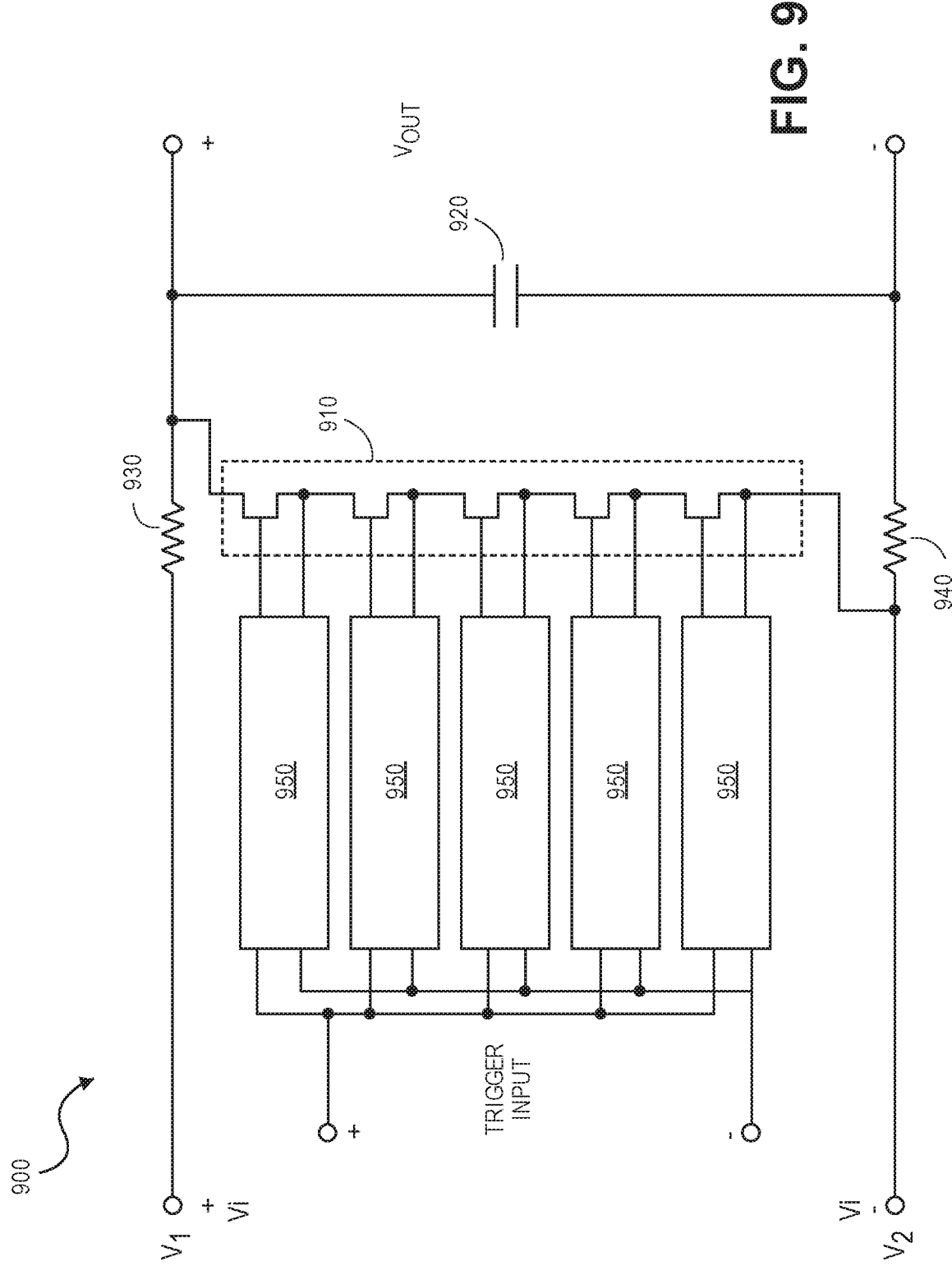
FIG. 9 is an electrical schematic of one of the pulse generator stages shown in FIG. 8.

FIG. 9 illustrates a pulse generator stage 900 which may be used as one of the pulse generator stages 810, 820, and 830 of pulse generator circuit 800 shown in FIG. 8.

Pulse generator stage 900 receives trigger pulses across input port trigger input, and generates output voltages at output port Vout in response to the received trigger pulses. The output voltages are also generated based on power voltages received at power input terminals V1 and V2. Pulse generator stage 900 includes multiple switch drivers 950. Pulse generator stage 900 also includes switch stack 910, capacitor 920, and resistors 930 and 940.

Switch drivers 950 are configured to receive the trigger pulses, and to generate control signals for the switches of switch stack 910 in response to the received trigger pulses, as discussed in further detail below. Each of the control signals is referenced to a voltage specific to the switch being driven. Accordingly, a first switch receives a control signal pulse between first and second voltages, and a second switch receives a control signal pulse between third and fourth voltages, where each of the first, second, third, and fourth voltages are different. In some embodiments, the difference between the first and second voltages is substantially the same as the difference between the third and fourth voltages.

Switch stack 910, capacitor 920, and resistors 930 and 940 cooperatively function with corresponding elements in the other pulse generator stages of pulse generator circuit 800, discussed above with reference to FIG. 8, to generate the voltage pulses across the positive and negative Vo output terminals of pulse generator circuit 800. These elements may, for example, cooperatively function as the corresponding elements discussed above with reference to pulse generator circuit 500 shown in FIGS. 5, 6A, and 6B. For example, these elements may cooperate to generate the voltage pulses across the positive and negative Vo output terminals of pulse generator circuit 800 in response to the power voltages applied to power input terminals V1 and V2 and to the control signals applied to the switches of switch stack 910.

Because the control signals are generated in response to the input pulses received across input port Vin of pulse generator circuit 700 illustrated in FIG. 7 through multiple stages of driving, the control signals cause all of the switches of the switch stacks of pulse generator circuit 700 to be turned on and to be turned off substantially simultaneously. For example, a 15V input pulse having a duration of, for example 100 ns, received at input port Vin of pulse generator circuit 700 may cause the pulse generator circuit 700 to generate a high-voltage (e.g. ~15 kV) output pulse having a duration of about 100 ns. Similarly, a 15V input pulse having a duration of, for example 5 µs, received at input port Vin of pulse generator circuit 700 may cause the pulse generator circuit 700 to generate a high-voltage (e.g. ~15 kV) output pulse having a duration of about 5 µs. Accordingly, the duration of the high-voltage output pulse is substantially the same as a selected duration of an input pulse.

Figure 10:
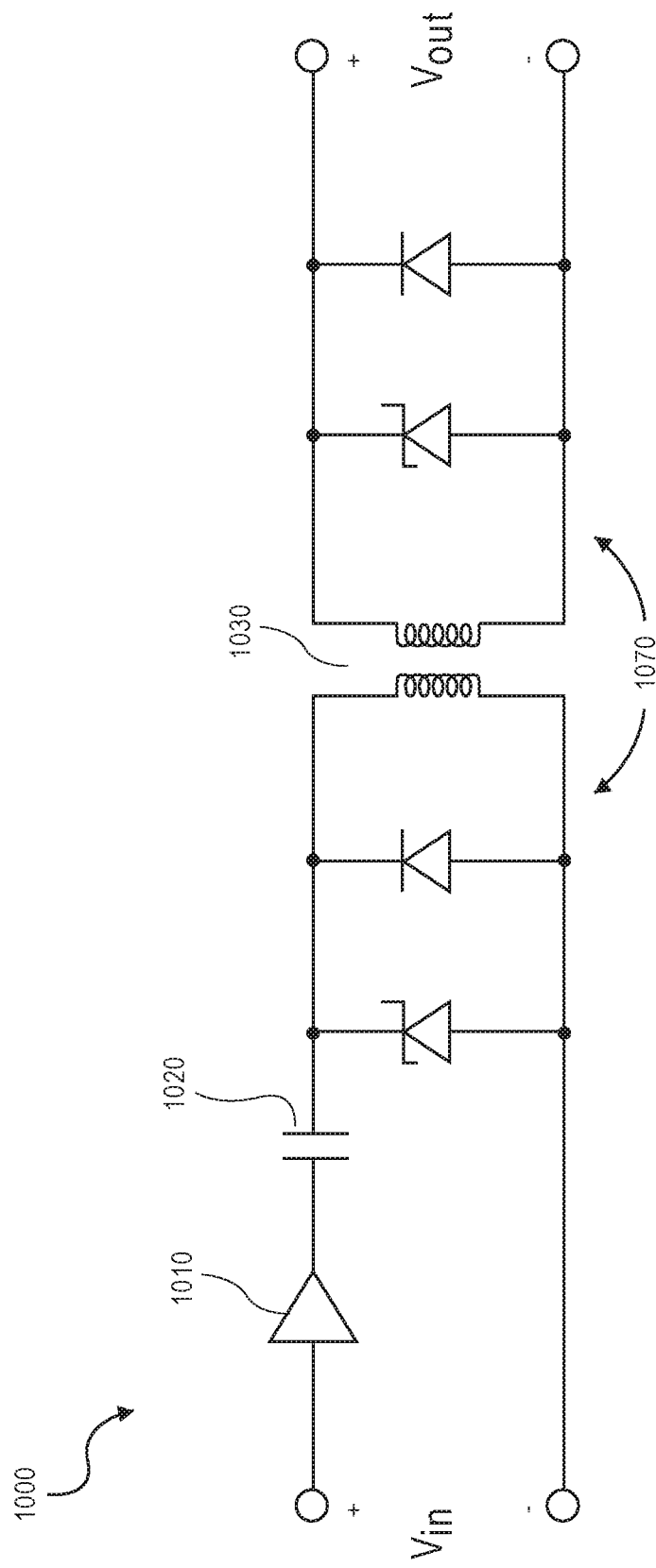
FIG. 10 is an electrical schematic of one of the switch drivers shown in FIG. 9.

FIG. 10 illustrates a switch driver 1000 which may be used as one of the switch drivers shown in FIG. 9.

Switch driver 1000 receives trigger pulses across input port Vin, and generates control signal pulses at output port Vout in response to the received trigger pulses. Switch driver 1000 includes amplifier circuit 1010, capacitor 1020, and transformer 1030. In some embodiments, switch driver 1000 also includes clamps circuits 1070.

Amplifier circuit 1010 receives the trigger pulses, and drives transformer 1030 through capacitor 1020, which reduces or blocks low frequency and DC signals. In response to being driven by amplifier circuit 1010, transformer 1030 generates control signal pulses at output port Vout, such that the duration of the control signal pulses is equal to or substantially equal (e.g. within 10% or 1%) to the duration of the trigger pulses at input port Vin.

In some embodiments, amplifier circuit 1010 includes multiple amplifier integrated circuits. For example, for increased current driving capability, multiple amplifier integrated circuits may be connected in parallel to form amplifier circuit 1010. For example, 2, 3, 4, 5, 6, 7, 8 or another number of amplifier integrated circuits may be used.

In some embodiments, clamp circuits 1070 are included at least to dampen potential signals, which may otherwise be caused by resonance. Clamp circuits 1070 include parallel diodes, which provide a short-circuit path for any current reversal, and also clamp the maximum voltage across the components connected to the clamp circuits 1070.

In some embodiments, the drivers 750, 850, and 1000 receive power from a DC-DC power module which is isolated from the power supply for the Marx generator. This ensures the cutoff of ground coupling.

In some embodiments, transformer 1030 has a 1:1 turns ratio. In alternative embodiments, a different turns ratio is used.

In some embodiments, in order to obtain very fast switching, the transformers 1030 has fewer than 5 turns in the primary winding and fewer than 5 turns in the secondary winding. For example, in some embodiments, the transformer 1030 has 1, 2, 3, or 4 turns in each of the primary and secondary windings. In some embodiments, the transformer 1030 has less than a complete turn, for example, ½ turn in the primary and secondary windings. The low number of turns in each of the primary and secondary windings allows for a low inductance loop and increases the current risetime in the secondary winding, which charges the input capacitance of the MOSFET switches.

Transformers for triggering MOSFETs in conventional applications require high coupling, high permeability, and a low-loss core in order to ensure current transfer efficiency. From pulse to pulse, the residual flux in the core needs to be cleared in order to avoid saturation when the transformer is operated at high frequency. Conventionally, a resetting circuit, which involves a third winding, to dissipate the core energy is used.

In some embodiments, lossy transformers, such as that typically used as an electromagnetic interference (EMI) choke to confine high frequency signals and dissipate their energy as heat are used to trigger the switches. For example, the transformers may have a voltage time constant less than 100 Vμs. In some embodiments, the Transformers have a voltage time constant less than 50 Vμs, 30 Vμs, 20 Vμs, 10 Vμs, or 5 Vμs. The use of the lossy transformer is contrary to the common practice in power electronics.

Although the high frequency flux is dampened due to the loss of the core (eddy loss, hysteresis loss, and resistive loss), the lossy transformers still allow sufficient confinement of the magnetic flux and provides sufficient coupling. In addition, the flux also decreases quickly in response to the signal on the primary winding being removed. The flux decay process usually takes approximately several microseconds.

Having such a transformer conventionally seems disadvantageous, but for coupling nanosecond to a few microsecond pulses, such a transformer is preferably used. Consequently, the following benefits are achieved: 1) high voltage, high frequency transient coupling from the high-voltage Marx generators to the low-voltage drivers is suppressed; 2) because of the loss in the transformer cores, the residual flux from previous pulses are dissipated faster than common low-loss transformer cores, such that the resetting winding is not needed and is not present.

A benefit of the switch driver 1000 is that it limits the output pulse duration. Because the switch control signals are generated by transformer 1030, even if circuitry generating the input trigger signals at input port Vin were to generate a pulse of indefinite length, the transformer would saturate, causing the control signals to turn off the switches.

Figure 11:
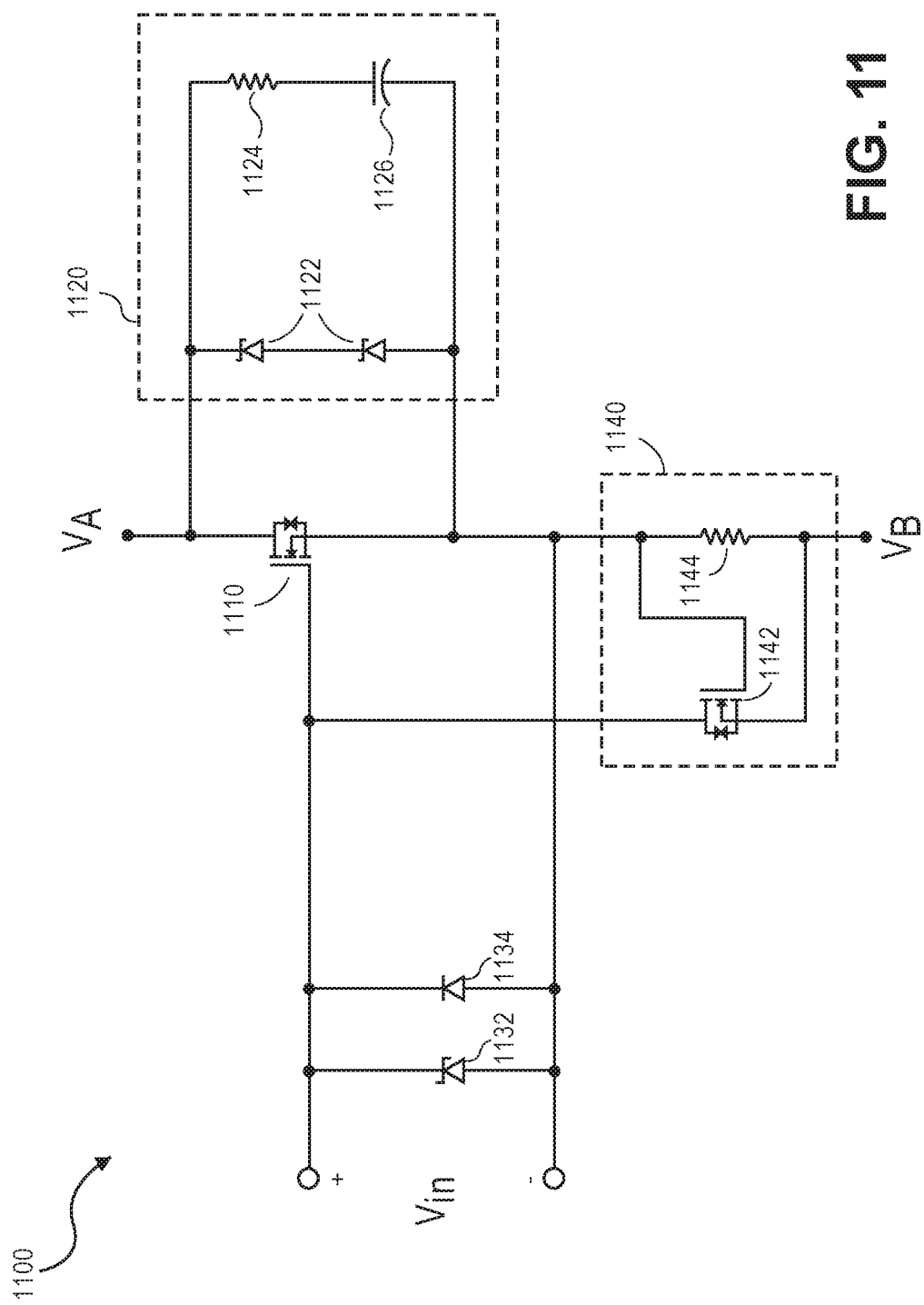
FIG. 11 is an electrical schematic of an alternative switch element.

FIG. 11 illustrates an example of a switch element 1100 comprising components which may be used in the switch stacks discussed here. Switch element 1100 includes switch 1110, and selectively forms a conductive or low resistance path between terminals VA and VB in response to a control voltage applied to input port Vin.

In some embodiments, switch 1110 is a transistor, such as a MOSFET. In some embodiments, switch 1110 is another type of switch. In some embodiments, switch 1110 has a turn on time of less than 5 ns, about 5 ns, about 10 ns, about 25 ns, about 15 ns, about 75 ns, about 100 ns, or greater than 100 ns.

In some embodiments, switch element 1100 also includes snubber circuit 1120. In some embodiments, the turn on times of the switches of the switch stacks are not identical. In order to prevent voltages greater than that which switch 1110 can tolerate, snubber circuit 1120 provides a current shunt path bypassing switch 1110. Diodes 1122 provide a low-frequency current path, and the combination of the capacitor 1126 and resistor 1124 provide a high-frequency current path.

In some embodiments, switch element 1100 also includes optional overcurrent protection circuit 1140. Overcurrent protection circuit 1140 includes switch 1142 and sense resistor 1144.

Current flowing from terminal VA to terminal VB is conducted through sense resistor 1144. Accordingly, a voltage is generated across sense resistor 1144 when the current flows from terminal VA to terminal VB. The generated voltage controls a conductive state of switch 1142. If the current flowing from terminal VA to terminal VB is greater than a threshold, the generated voltage causes the switch 1142 to conduct. As a result, switch 1142 reduces the control voltage of switch 1110. In response to the reduced control voltage, switch 1110 becomes less conductive or turns off. Consequently, the current which may be conducted from terminal VA to terminal VB is limited by overcurrent protection circuit 1140.

In some embodiments, a current limiting resistor is placed between the gate of switch 1110 and the drain of switch 1142 to prevent switch 1142 from experiencing current greater than that which would cause damage.

In the embodiments discussed herein, MOSFET switches are used. In alternative embodiments, other switches are used. For example, in some embodiments, thyristors, IGBTs or other semiconductor switches are used.

Figure 12:
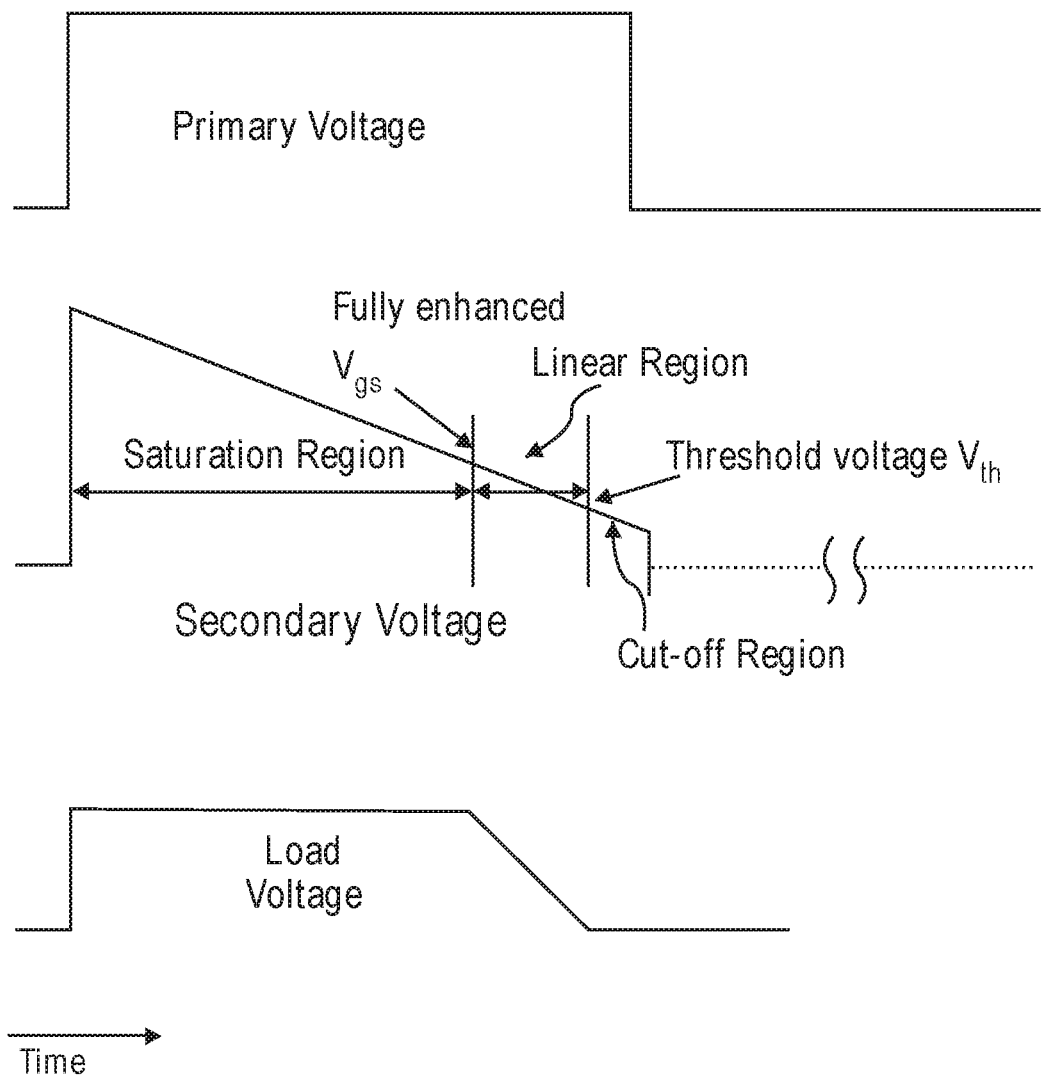
FIG. 12 is a waveform diagram illustrating the operation of a transformer and a control voltage to a MOSFET gate.

An example of the operation of the transformer is illustrated in FIG. 12. The voltage at the input primary inductor is substantially a square waveform, but the voltage at the secondary inductor, which is the MOSFET's gate-source voltage, tapers as the voltage magnitude decreases toward zero, for example, within a period of several microseconds. After a reduction in voltage at the secondary inductor due to transformer saturation, the switch receiving the voltage enters a linear region of operation from a saturation region of operation when the voltage is lower than the fully enhanced Vgs. As a result, the resistance of the switch increases and the output voltage across the load also shows a tapered profile. When the voltage at the secondary inductor decreases to a value less than the turn-on threshold of a MOSFET (Vth), the MOSFET will be shut off. Once the MOSFET is off, even if the duration of the trigger signal is extended, the switch no longer conducts and can be considered an open circuit. The waveform of the voltage at the secondary inductor therefore limits the duration of high voltage output pulses from each panel, for example, to be several microseconds or less.

In some embodiments, the duration of the trigger signal is short enough that the switches remain in saturation because the reduction in voltage at the secondary inductor is insufficient to cause the switches to enter linear region operation. In such embodiments, the load voltage pulses do not exhibit the tapering illustrated in FIG. 12. For example, in such embodiments the load voltage pulses may be substantially square.

In some embodiments, the switch stacks discussed herein include switches, as discussed above, as well as other components.

In some embodiments, when generating pulses of a duration less than a threshold, the shape of the pulses are substantially square. In some embodiments, when generating pulses of the duration greater than a threshold, the shape of the pulses are substantially square for a duration substantially equal (e.g. within 10% or 1%) to the threshold. During the time after the threshold, the voltage of such long pulses drops toward 0 V. In some embodiments, the drop toward 0 V is substantially linear. In some embodiments, the drop toward 0 V is substantially exponential.

Figure 13:
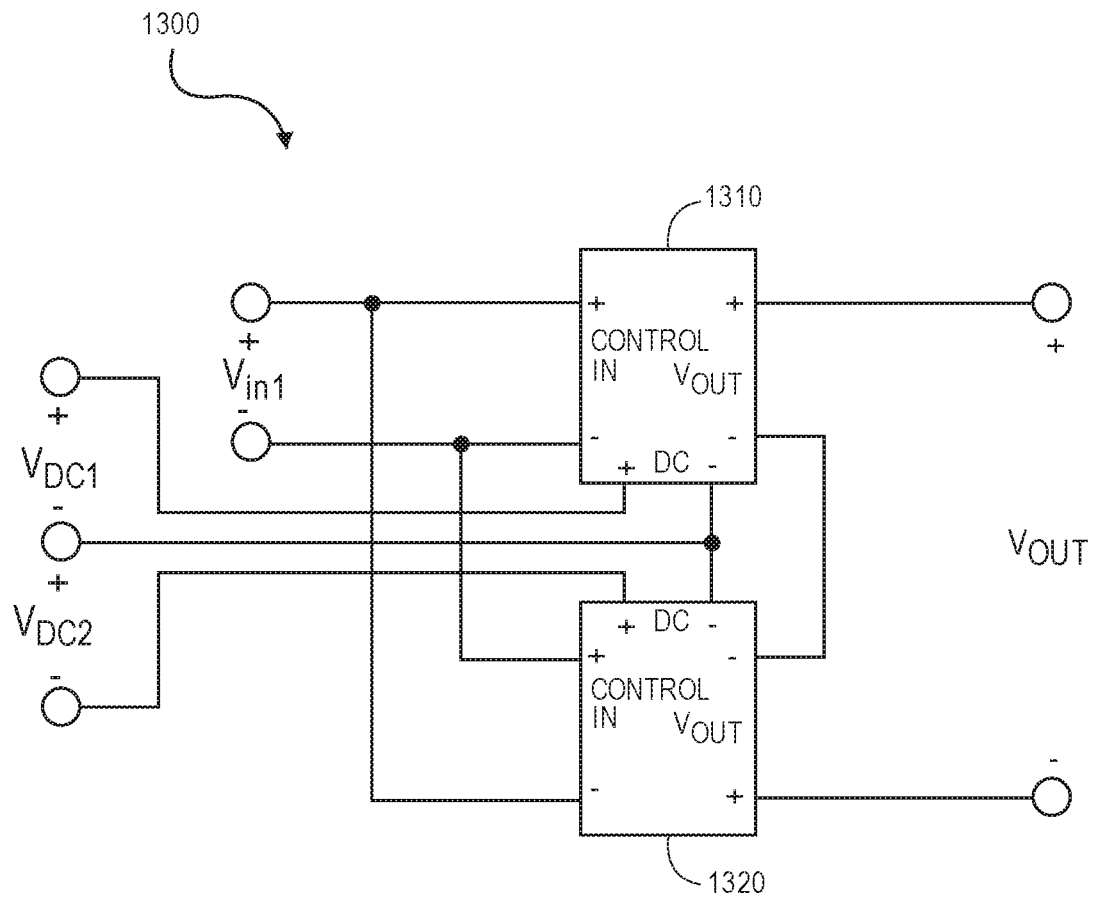
FIG. 13 is an alternative electrical schematic of a pulse generator shown in FIG. 1.

FIG. 13 illustrates an alternative pulse generator circuit 1300 which may be used inside nsPEF system 100 of FIG. 1.

Pulse generator circuit 1300 receives input pulses across input port Vin and DC voltages at input ports VDC1 and VDC2, and generates output pulses across output port Vout in response to the received input pulses and DC voltages.

Pulse generator circuit 1300 includes multiple pulse generator circuits 1310 and 1320. In this embodiment, two pulse generator circuits are used. In alternative embodiments, more pulse generator circuits are used. For example, in some embodiments, 3, 4, 5, 10 or another number of pulse generator circuits having their output ports serially connected, as discussed below with reference to pulse generator circuit 1300, are used.

Each of pulse generator circuits 1310 and 1320 may be similar to the other pulse generator circuits discussed herein. For example pulse generator circuits 1310 and 1320 may be similar to or may be substantially identical to pulse generator circuit 700 discussed above with reference to FIG. 7.

Each of pulse generator circuits 1310 and 1320 receive the same input pulse signal across their respective Control In input ports. In response, each of pulse generator circuits 1310 and 1320 generate high voltage pulses across their respective Vout output ports. Because the Vout output ports of pulse generator circuits 1310 1320 are serially connected, the voltage pulse generated by pulse generator circuits 1310 and 1320 across output port Vout of pulse generator circuit 1300 is substantially equal (e.g. within 10% or 1%) to the sum of the voltages of the pulses respectively generated by pulse generator circuits 1310 and 1320.

Figure 14:
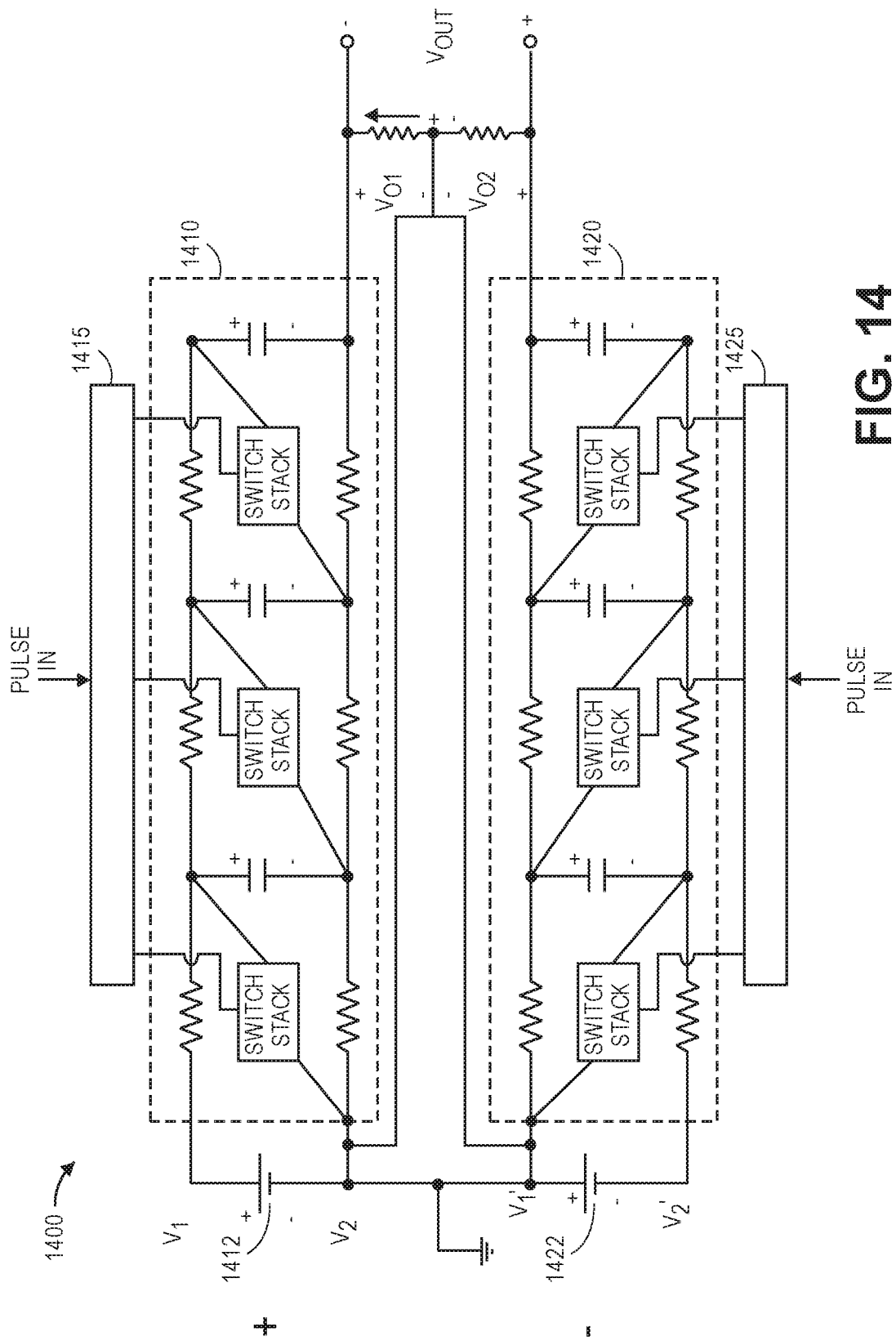
FIG. 14 is an alternative electrical schematic of a pulse generator shown in FIG. 1.

FIG. 14 illustrates an alternative pulse generator circuit 1400 which may be used inside nsPEF system 100 of FIG. 1, and which has characteristics similar to the pulse generator 1300 of FIG. 13. Pulse generator circuit 1400 includes pulse generators 1410 and 1420, drivers 1415 and 1425, and power supplies 1412 and 1422.

Pulse generator circuit 1400 includes multiple pulse generator circuits 1410 and 1420. In this embodiment, two pulse generator circuits are used. In alternative embodiments, more pulse generator circuits are used. Each of pulse generator circuits 1410 and 1420 may be similar to the other pulse generator circuits discussed herein.

Pulse generator circuit 1400 receives input pulses at each of drivers 1415 and 1425, which may be similar to driver 850 discussed above with reference to FIG. 8. Pulse generator circuit 1400 generates output pulses across output port Vout in response to the received input pulses. The output voltage pulses are also based on power voltages received from power supplies 1412 and 1422.

Each of drivers 1415 and 1425 receive an input pulse signal. In response to the received input signals, drivers 1415 and 1425 respectively generate driving signal pulses for pulse generator circuits 1410 and 1420. In response to the driving signal pulses, each of pulse generator circuits 1410 and 1420 generate high voltage pulses across their respective output ports Vo1 and Vo2. Because the Vo1 and Vo2 output ports of pulse generator circuits 1410 and 1420 are serially connected, the voltage pulse generated by pulse generator circuits 1410 and 1420 across output port Vout of pulse generator circuit 1400 is substantially equal (e.g. within 10% or 1%) to the sum of the voltages of the pulses respectively generated by pulse generator circuits 1410 and 1420.

In this embodiment, pulse generator circuit 1410 generates a high voltage pulse across its output port Vo1 which is substantially equal (e.g. within 10% or 1%) to three times the voltage of power supply 1412, $(-3 \times [V1-V2])$. In addition, pulse generator circuit 1420 generates a high voltage pulse across its output port Vo2 which is substantially equal (e.g. within 10% or 1%) to three times the voltage of power supply 1414 $(3 \times [V'1-V'2])$. As a result, pulse generator circuit 1400 generates a voltage of $(3 \times [V'1-V'2]) - (-3 \times [V1-V2])$ across its output port Vout.

In some embodiments, a single driver circuit connected to both pulse generator circuit 1410 and 1420 is used instead of drivers 1415 and 1425. In such embodiments, the single driver circuit generates driving signal pulses for both pulse generator circuits 1410 and 1420 in response to an input pulse signal.

For various purposes, it may be desirable to discharge the capacitors which are used by a pulse generator to generate pulses. For example, it may be desirable to discharge capacitor 920 of the pulse generator stage 900 of FIG. 9. Discharging the capacitors may be done using various embodiments of various discharge circuits. Some embodiments are discussed herein.

Figure 15:
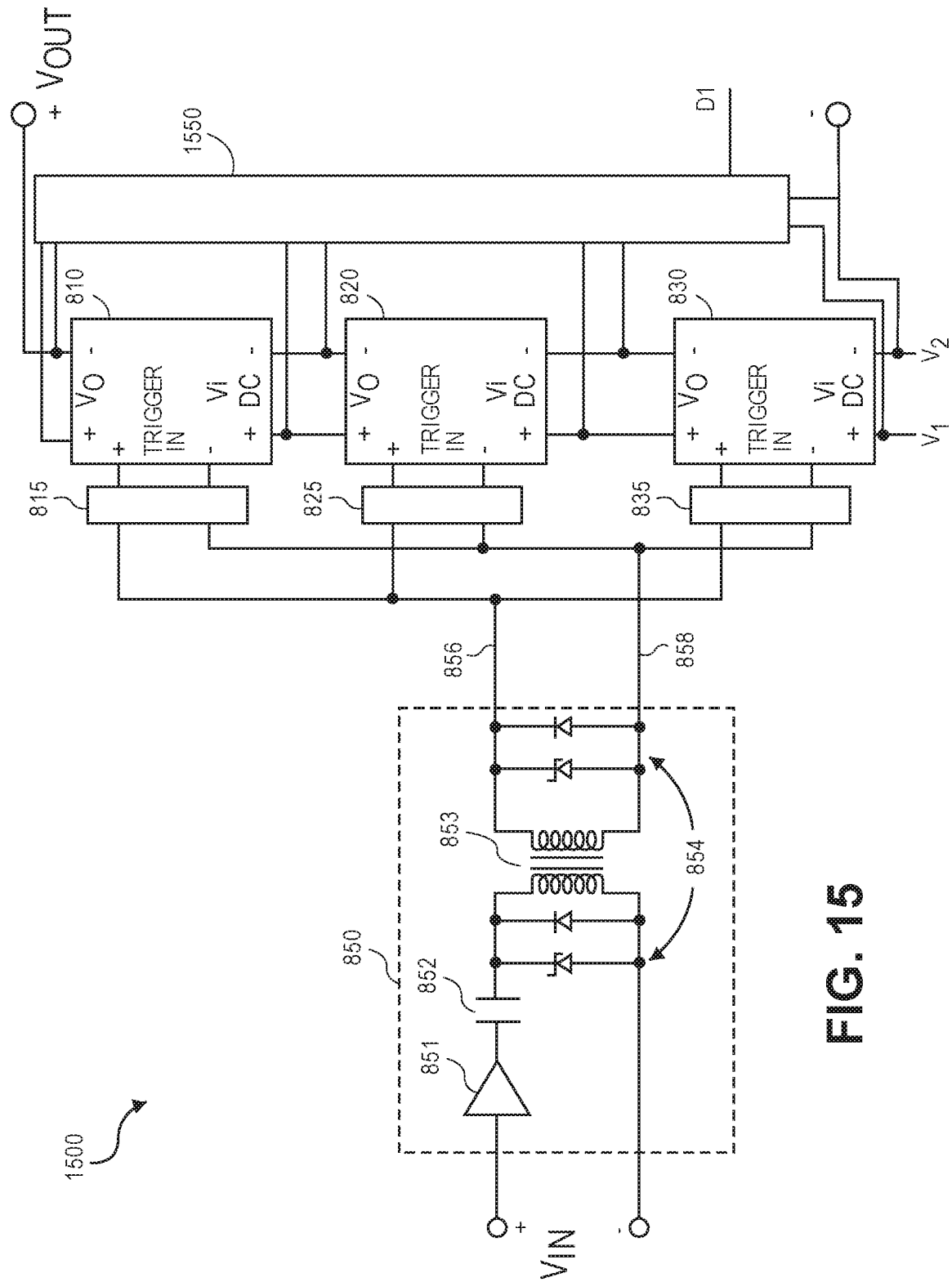
FIG. 15 is an electrical schematic of an embodiment of one of the pulse generator circuits shown in FIG. 7 having a discharge circuit.

FIG. 15 illustrates a pulse generator circuit 1500 which may be used for pulse generator circuits 710, 720, 730, and 740 of pulse generator circuit 700 of FIG. 7. Pulse generator circuit 1500 is similar to pulse generator circuit 800 illustrated in FIG. 8. Pulse generator circuit 1500 additionally includes a particular discharge circuit 1550.

As shown, discharge circuit 1550 is electrically connected to first and second power supply input terminals V1 and V2. Discharge circuit 1550 is also electrically connected to discharge input terminal D1. Based on voltages at the first and second power supply input terminals V1 and V2 and discharge input terminal D1, discharge circuit 1550 selectively discharges each of the pulse generator stages 810, 820, and 830.

In some embodiments, discharge circuit 1550 is configured to discharge each of the pulse generator stages 810, 820, and 830 in response to a discharge control signal received at discharge input terminal D1. In some embodiments, discharge circuit 1550 is configured to respectively discharge each of the pulse generator stages 810, 820, and 830 in response to a comparison of the charging voltage as determined by the voltages at first and second power supply input terminals V1 and V2 and the charged voltage stored on the capacitor of each of the pulse generator stages 810, 820, and 830.

Figure 16:
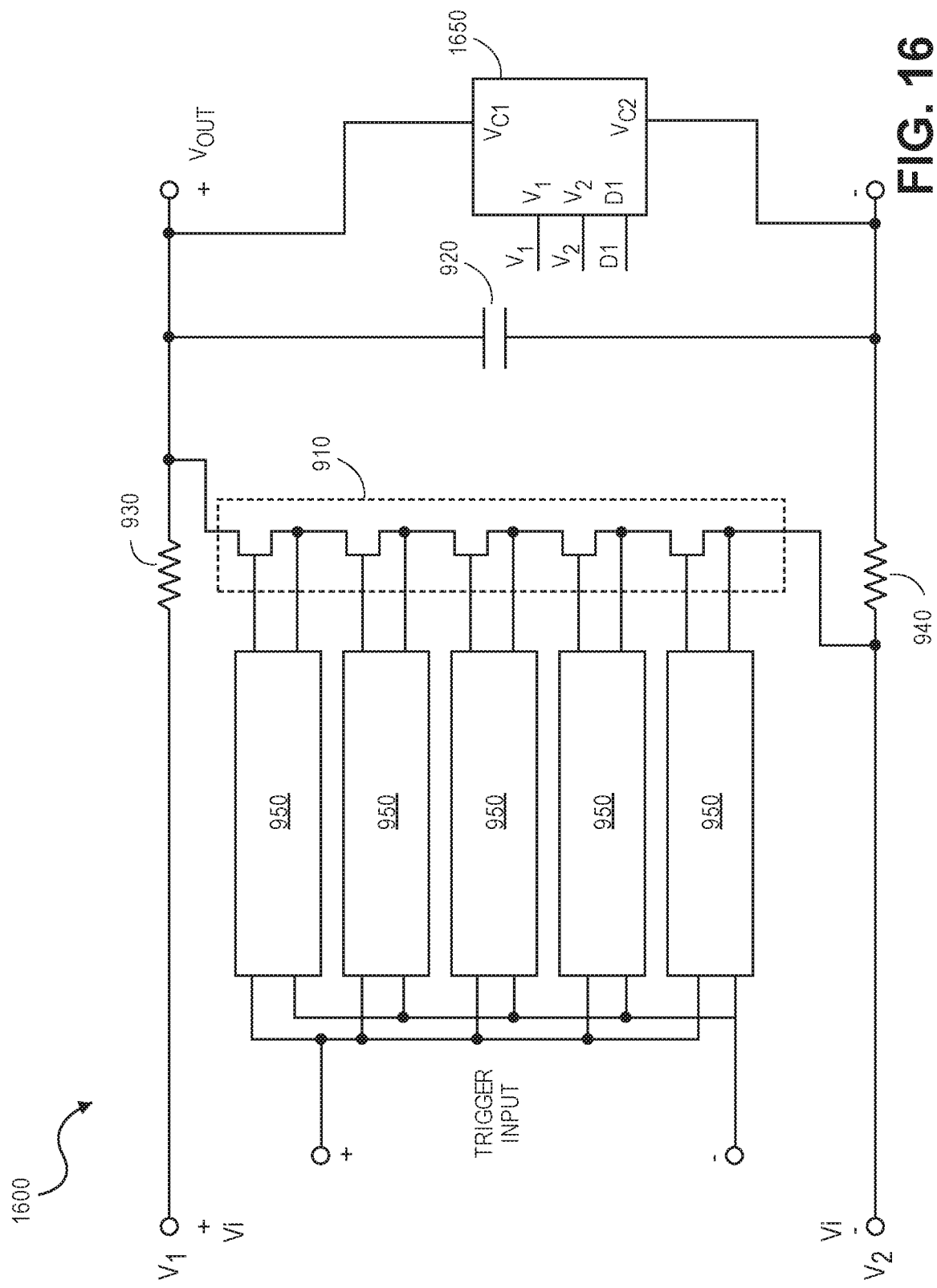
FIG. 16 is an electrical schematic of an embodiment of one of the pulse generator stages shown in FIG. 15 having a discharge circuit stage.

FIG. 16 illustrates a pulse generator stage 1600 which may be used as one of the pulse generator stages 810, 820, and 830 of pulse generator circuit 1500 shown in FIG. 15. Pulse generator stage 1600 includes a discharge circuit stage 1650.

In some embodiments, discharge circuit stage 1650 is configured to discharge capacitor 920 in response to a discharge command signal received at discharge input terminal D1. In some embodiments, discharge circuit stage 1650 is configured to discharge capacitor 920 in response to a comparison of the charging voltage as determined by the voltages at first and second power supply input terminals V1 and V2 and the charged voltage stored on the capacitor 920.

Figure 17:
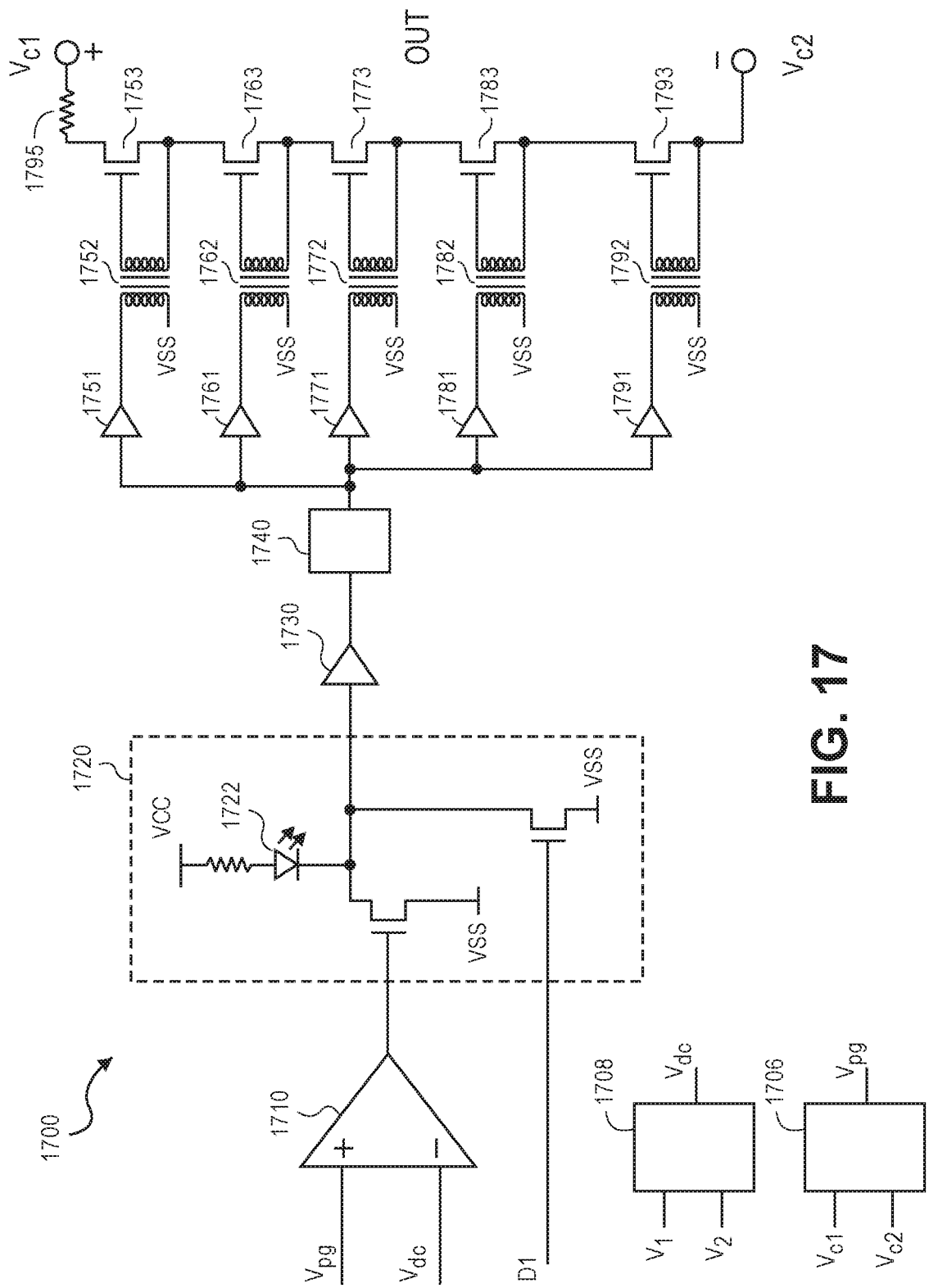
FIG. 17 is a schematic illustration of an embodiment of a discharge circuit stage used in the pulse generator stage of FIG. 16.

FIG. 17 is a schematic illustration of an embodiment of a discharge circuit stage 1700 used in the pulse generator stage 1600 of FIG. 16. Pulse generator stage 1700 includes voltage generators 1706 and 1708, comparator 1710, OR circuit 1720, buffer 1730, pulse generator 1740, buffers 1751, 1761, 1771, 1781, and 1791, transformers 1752, 1762, 1772, 1782, and 1792, switches 1753, 1763, 1773, 1783, and 1793, and resistor 1795.

Comparator 1710 is configured to generate a signal which selectively causes the other components of discharge circuit stage 1700 to cause switches 1753, 1763, 1773, 1783, and 1793, to become conductive and to effectively short out the discharge terminals at output port OUT. Using multiple switches has the benefit of allowing for voltages at the output of discharge circuit stage 1700 to be greater than the maximum drain/source voltage rating of a single switch. For example, in the illustrated embodiment, five switches are used. If the maximum drain/source voltage rating for each switch is 1000 V, using five switches ideally allows for 5000 V at the output of discharge circuit stage 1700.

For example, in this embodiment, comparator 1710 receives input voltages at voltage control input terminals Vpg and Vdc. The voltage at voltage input terminal Vpg is generated by voltage generator 1706 based on the voltage across the capacitor to be selectively discharged by discharge circuit stage 1700. The voltage at voltage input terminal the Vdc is generated by voltage generator 1708 based on the voltages of the first and second power supply input terminals V1 and V2.

In some embodiments, voltage generators 1706 and 1708 are level shift circuits which receive voltages which are higher than that which comparator 1710 is able to withstand. For example, voltage generator 1706 may be configured to receive a voltage difference across its inputs Vc1 and Vc2 of about 5 kV, and to generate an output voltage on terminal Vpg equal to about 10 V, where the output voltage on terminal Vpg is proportional to the voltage difference across inputs Vc1 and Vc2. Similarly, voltage generator 1708 may be configured to receive a voltage difference across its inputs V1 and V2 of about 5 kV, and to generate an output voltage on terminal Vdc equal to about 10 V, where the output voltage on terminal Vdc is proportional to the voltage difference across inputs V1 and V2.

In some embodiments, the proportionality constant relating the voltage on terminal Vpg to the voltages across inputs Vc1 and Vc2 is equal to the proportionality constant relating the voltage on terminal Vdc to the voltages across inputs V1 and V2. In such embodiments, comparator 1710 is configured to cause switches 1753, 1763, 1773, 1783, and 1793, to become conductive and provide a discharge path across the output port OUT in response to the DC input voltage across terminals V1 and V2 of pulse generator stage 1600 being less than the voltage across capacitor 920 of pulse generator stage 1600.

In some embodiments, the proportionality constant relating the voltage on terminal Vpg to the voltages across inputs Vc1 and Vc2 is not equal to the proportionality constant relating the voltage on terminal Vdc to the voltages across inputs V1 and V2. In such embodiments, comparator 1710 is configured to cause switches 1753, 1763, 1773, 1783, and 1793, to become conductive and to effectively short out the output port OUT in response to the DC input voltage across terminals V1 and V2 of pulse generator stage 1600 being less than the voltage across capacitor 920 of pulse generator stage 1600 by more than a predetermined threshold related to the difference in the proportionality constants.

For example, in some embodiments, a voltage difference of 5 kV across input terminals V1 and V2 causes voltage generator 1708 to generate a voltage of 10 V at terminal Vdc, and a voltage difference of 5.1 kV across input terminals Vc1 and Vc2 causes voltage generator 1706 to generate a voltage of 10 V at terminal Vpg. In such embodiments, comparator 1710 is configured to cause switches 1753, 1763, 1773, 1783, and 1793 to become conductive and to effectively short out the output port OUT in response to the DC input voltage across terminals V1 and V2 of pulse generator stage 1600 being more than 100 V less than the voltage across capacitor 920 of pulse generator stage 1600.

In some embodiments, voltage generators 1706 and 1708 are resistive voltage dividers, each comprising first and second resistive elements serially connected. The output voltage is generated at the node shared by the first and second resistive elements, and first and second input voltages are respectively connected with one of the first and second resistive elements.

OR circuit 1720 is configured to selectively generate a signal which causes switches 1753, 1763, 1773, 1783, and 1793 to become conductive and to effectively short out the output port OUT in response to the DC input voltage across terminals V1 and V2 of pulse generator stage 1600. OR circuit 1720 is configured to generate the signal based on the output of comparator 1710 and on the voltage level applied at discharge control input terminal D1.

In this embodiment, OR circuit 1720 is configured to causes switches 1753, 1763, 1773, 1783, and 1793 to become conductive in response to either the output of comparator 1710 or the voltage level at discharge input terminal D1 being greater than a threshold. For example, if either the output of comparator 1710 or the voltage level at discharge input terminal D1 is greater than the threshold, if either the output of comparator 1710 or the voltage level at discharge input terminal D1 is greater than the threshold, the output of OR circuit 1720 causes switches 1753, 1763, 1773, 1783, and 1793 to become conductive.

In this embodiment, OR circuit 1720 includes light emitting diode (LED) 1722, which is configured to emit light when either the output of comparator 1710 or the voltage level at discharge input terminal D1 is greater than the threshold. Accordingly, LED 1722 provides a visual indication that the discharge circuit stage 1700 is discharging the capacitor 920 of pulse generator stage 1600.

Discharge circuit stage 1700 optionally includes buffer 1730. The buffer 1730 receives the signal generated by OR circuit 1720, and generates an output signal for pulse generator 1740.

In some embodiments, buffer 1730 is not used. In such embodiments, the signal generated by OR circuit 1720 may be provided directly to pulse signal generator 1740, or may be conditioned by other circuitry, which provides a signal to pulse signal generator 1740 based on the signal generated by OR circuit 1720.

In some embodiments, buffer 1730 is an inverting buffer. In some embodiments, buffer 1730 is a non-inverting buffer.

In this embodiment, pulse signal generator 1740 is configured to receive the signal from buffer 1730. In response to the received signal, pulse signal generator 1740 selectively generates a series of pulse signals based on the received signal. In some embodiments, the received signal is received by an enable input, such that pulse signal generator 1740 generates the series of pulse signals in response to the received signal being of an appropriate logic state, and does not generate the series of pulse signals in response to the received signal being of an opposite logic state.

In some embodiments, pulse signal generator 1740 includes a timer circuit, such as a 555 timer. In such embodiments, the timer circuit may be configured to generate pulse signals appropriate for causing switches 1753, 1763, 1773, 1783, and 1793 to become conductive. For example, timer circuit may be tuned so as to generate a series of pulse signals which are appropriate for transformers 1752, 1762, 1772, 1782, and 1792, such that transformers 1752, 1762, 1772, 1782, and 1792 do not saturate and such that transformers 1752, 1762, 1772, 1782, and 1792 generate signals which cause switches 1753, 1763, 1773, 1783, and 1793 to be conductive for a large portion of each period of the pulse signal series. For example, frequency, duty cycle, rise time, and fall time may be tuned to avoid saturation of the transformers 1752, 1762, 1772, 1782, and 1792, and may be tuned to increase or maximize the portion of each period during which switches 1753, 1763, 1773, 1783, and 1793 are conductive.

Discharge circuit stage 1700 optionally includes buffers 1751, 1761, 1771, 1781, and 1791. The buffers 1751, 1761, 1771, 1781, and 1791 receive the series of pulse signals generated by pulse signal generator 1740, and respectively generate signals for transformers 1752, 1762, 1772, 1782, and 1792.

In some embodiments, buffers 1751, 1761, 1771, 1781, and 1791 are not used. In such embodiments, the signal generated by pulse signal generator 1740 may be provided directly to the transformers 1752, 1762, 1772, 1782, and 1792, or may be conditioned by other circuitry, which provides a signal to the transformers 1752, 1762, 1772, 1782, and 1792 based on the signal generated by pulse signal generator 1740.

In some embodiments, buffers 1751, 1761, 1771, 1781, and 1791 are inverting buffers. In some embodiments, buffers 1751, 1761, 1771, 1781, and 1791 are non-inverting buffers.

In this embodiment, transformers 1752, 1762, 1772, 1782, and 1792 are configured to receive the pulse signal series from buffers 1751, 1761, 1771, 1781, and 1791. In response to the received pulse signal series, transformers 1752, 1762, 1772, 1782, and 1792 selectively generates a series of pulses based on the received pulse signal series. The series of pulse signals generated by transformers 1752, 1762, 1772, 1782, and 1792 respectively cause switches 1753, 1763, 1773, 1783, and 1793 to become conductive and to effectively short out the output port OUT.

For example, switches 1753, 1763, 1773, 1783, and 1793 may be transistors, and in response to the received pulse signal series, each of transformers 1752, 1762, 1772, 1782, and 1792 may be configured to generate a gate voltage and a source voltage for a corresponding one of the transistors 1753, 1763, 1773, 1783, and 1793. Because of the floating output of the transformers 1752, 1762, 1772, 1782, and 1792, the gate voltages are generated so as to be referenced to the corresponding source voltages. In some embodiments, bipolar transistors may be used and the transformers 1752, 1762, 1772, 1782, and 1792 may be configured to generate a base voltage and an emitter voltage for a corresponding one of the transistors 1753, 1763, 1773, 1783, and 1793.

Figure 18:
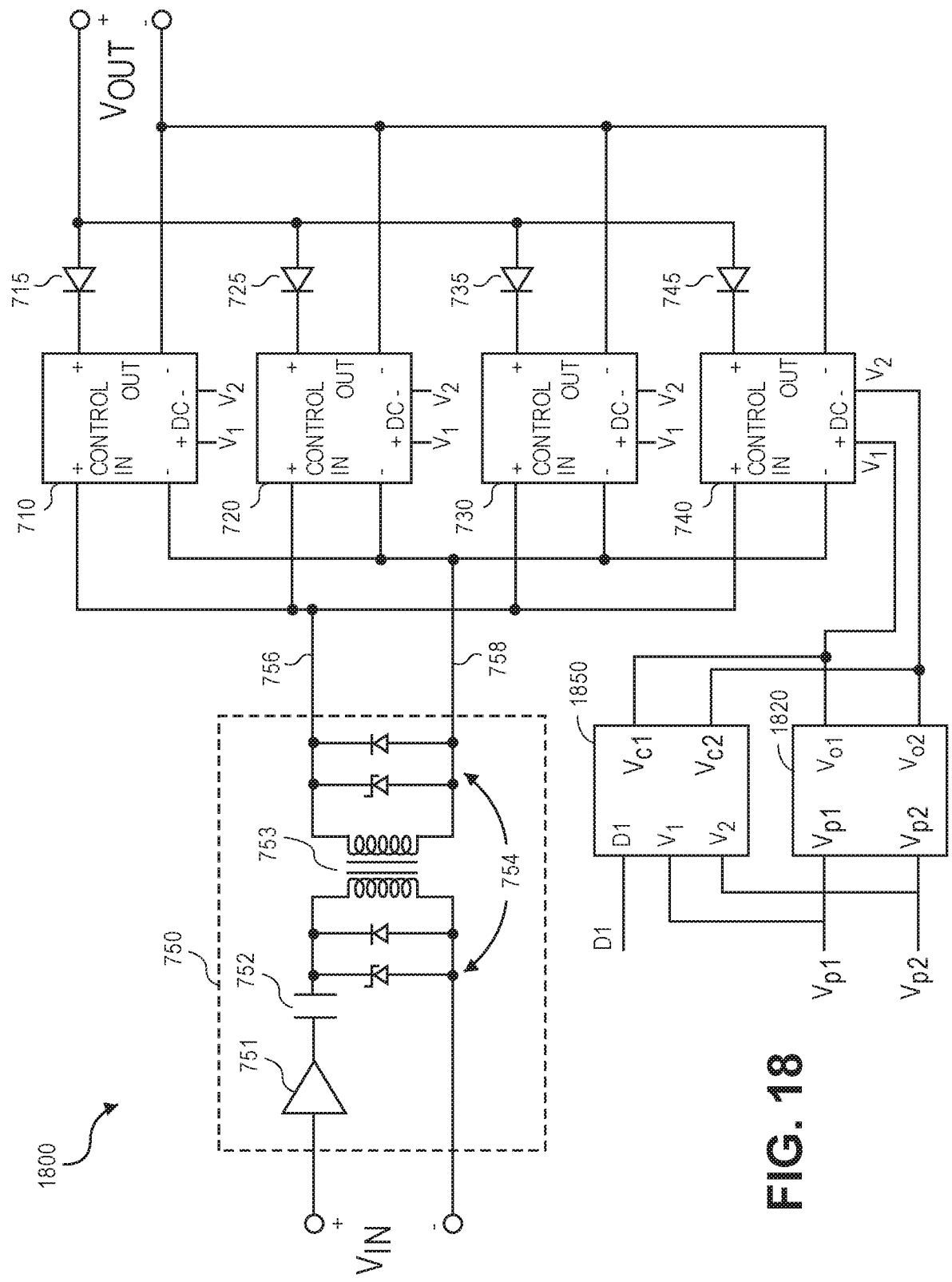
FIG. 18 is an electrical schematic of an embodiment a pulse generator circuit having a discharge circuit.

FIG. 18 illustrates an alternative pulse generator circuit 1800 which may be used for pulse generator circuit 700 of FIG. 7. Pulse generator circuit 1800 is similar to pulse generator circuit 700 illustrated in FIG. 7. Pulse generator circuit 1800 additionally includes a discharge circuit 1850 and a peak voltage source 1820.

As shown, discharge circuit 1850 is electrically connected to first and second power supply input terminals VP1 and VP2. Discharge circuit 1850 is also electrically connected to discharge input terminal D1. Based on voltages at the first and second power supply input terminals VP1 and VP2, discharge input terminal D1, and first and second power supply terminals V1 and V2, discharge circuit 1850 selectively discharges first and second power supply terminals V1 and V2.

In some embodiments, discharge circuit 1850 is configured to discharge first and second power supply terminals V1 and V2 in response to a discharge control signal received at discharge input terminal D1. In some embodiments, discharge circuit 1850 is configured to discharge the first and second power supply terminals V1 and V2 in response to a comparison of the charging voltage as determined by the voltages at first and second power supply terminals V1 and V2 and the voltage of the first and second power supply input terminals VP1 and VP2.

Discharge circuit stage 1700 of FIG. 17, or any of the other discharge circuits discussed herein may be used as discharge circuit 1850.

Peak voltage source 1820 may be any low-pass filter. For example, peak voltage source 1820 may include a resistor and a capacitor to form a single pole RC filter. Other filters may additionally or alternatively be used.

Figure 19:
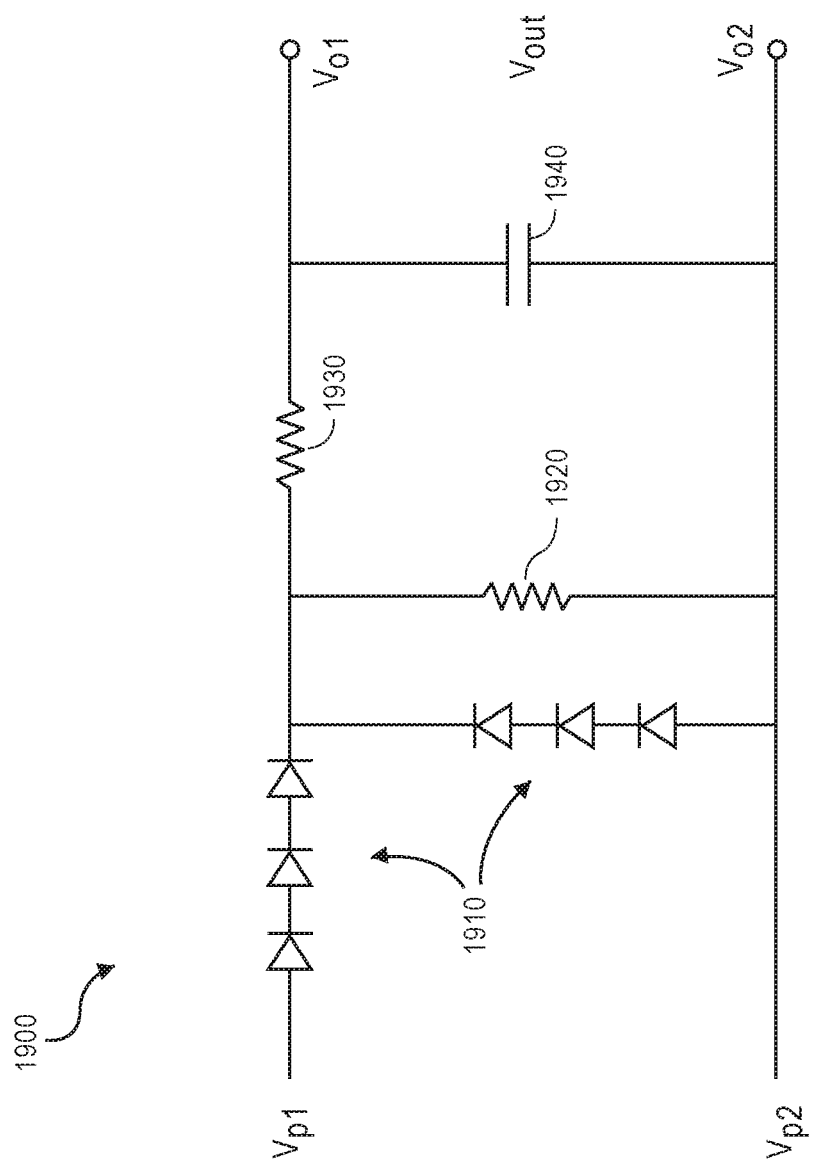
FIG. 19 is an illustration of an embodiment of a peak voltage source.

FIG. 19 is an embodiment of a peak voltage source 1900, which may be used as peak voltage source 1820 of FIG. 18. As shown, peak voltage source 1900 includes diodes 1910, resistor 1920, RC resistor 1930, and RC capacitor 1940. Resistor 1920 operates to passively discharge capacitor 1940 and power supply terminals V1 and V2.

Figure 20A:
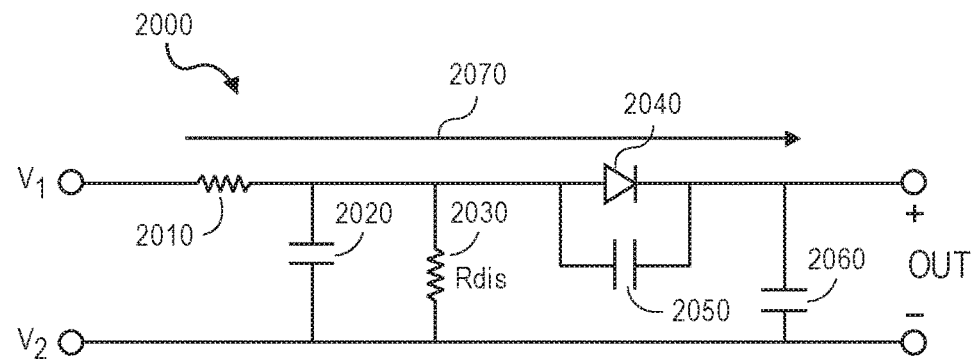
FIGS. 20A and 20B are schematic illustrations of an embodiment of a discharge circuit stage used in the pulse generator stage of FIG. 16.
Figure 20B:
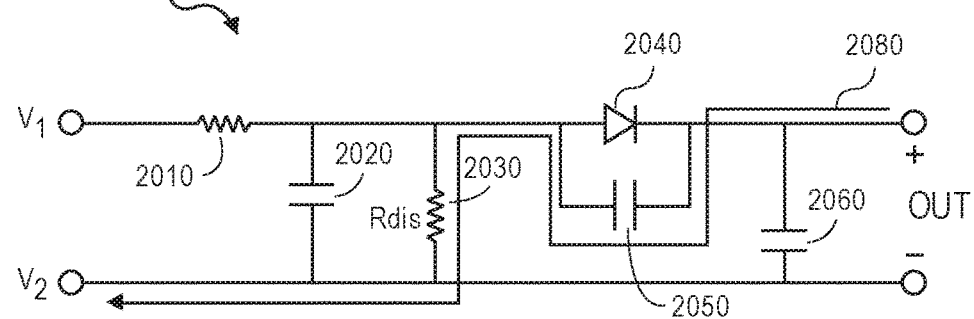

FIGS. 20A and 20B are schematic illustrations of an alternative embodiment of a discharge circuit stage 2000 which may be used as or in a discharge circuit for a pulse generator as described herein or for pulse generators of other topologies. For example, discharge circuit stage 2000 may be used as the discharge circuit stage 1650 in the pulse generator stage 1600 of FIG. 16. An instance of discharge circuit stage 2000 is used to interface between each pulse generator stage and the power supply used to charge the pulse generator stages. Discharge circuit stage 2000 includes series resistor 2010, comparing capacitor 2020, discharge resistor 2030, blocking diode 2040, bridge capacitor 2050, and buffering capacitor 2060.

FIG. 20A includes an indication 2070 of the current path from the power supply to the pulse generator stage while the pulse generator stage is being charged by the power supply. As shown, while the pulse generator stage is being charged, the current flows from the power supply through series resistor 2010, through blocking diode 2040, to the output port OUT, and to the pulse generator stage being charged (not shown). The pulse generator stage is charged in response to the power supply input voltage being greater than the voltage of the pulse generator stage by at least a forward voltage drop of the blocking diode 2040.

FIG. 20B includes an indication 2080 of the current path from the pulse generator stage to the power supply while the pulse generator stage is being discharged by discharge circuit 2000 and by the power supply. As shown, while the pulse generator stage is being discharged, the current flows from the output port OUT, and is coupled through bridge capacitor 2050, through passive discharge resistor 2030, and to power supply terminal V2. The pulse generator stage is discharged in response to the voltage of the power supply input voltage dropping to a voltage less than the voltage of the pulse generator stage.

In this embodiment, the discharge resistor 2030 serves as a passive continuous bleed resistor, and contributes to providing a path for current from the pulse generator stage to the power supply in order to discharge the pulse generator stage.

In some embodiments, discharge circuit stage 2000 may be used as discharge circuit 1850 of FIG. 18.

Figure 21A:
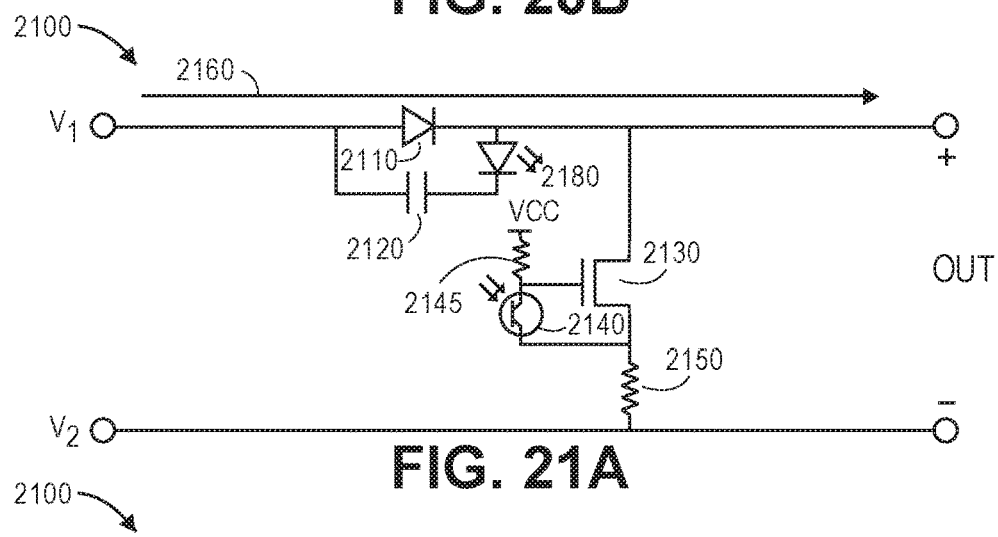
FIGS. 21A and 21B are schematic illustrations of an embodiment of a discharge circuit stage used in the pulse generator stage of FIG. 16.
Figure 21B:
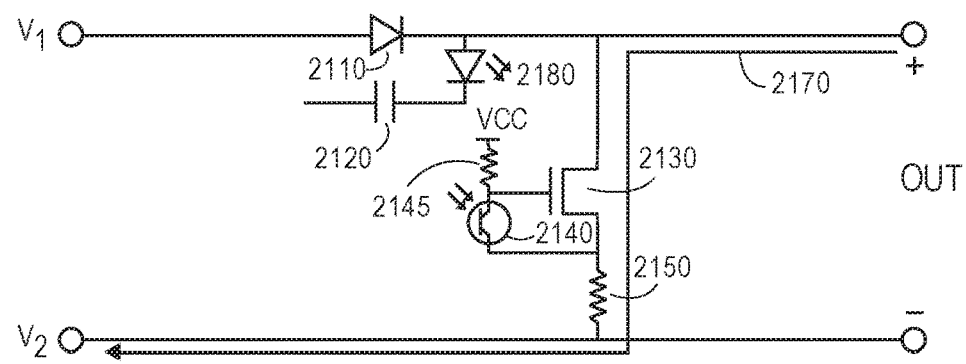

FIGS. 21A and 21B are schematic illustrations of an alternative embodiment of a discharge circuit stage 2100 which may be used as or in a discharge circuit for a pulse generator as described herein or for pulse generators of other topologies. For example, discharge circuit stage 2100 may be used in the pulse generator stage 1600 of FIG. 16. An instance of discharge circuit stage 2100 is used to interface between each pulse generator stage and the power supply used to charge the pulse generator stages. Discharge circuit stage 2100 includes blocking diode 2110, bridge capacitor 2120, LED 2180, current limiting resistor 2145 connected to power supply Vcc, switch 2130, phototransistor 2140, and discharge resistor 2150. In some embodiments, capacitor 2120 is not used and the cathode of LED 2180 is connected to the anode of blocking diode 2110.

FIG. 21A includes an indication 2160 of the current path from the power supply to the pulse generator stage while the pulse generator stage is being charged by the power supply. As shown, while the pulse generator stage is being charged, the current flows from the power supply through blocking diode 2110, to the output port OUT, and to the pulse generator stage being charged (not shown). The pulse generator stage is charged in response to the power supply input voltage being greater than the voltage of the pulse generator stage by at least a forward voltage drop of the blocking diode 2110.

FIG. 21B includes an indication 2170 of the current path from the pulse generator stage to the power supply while the pulse generator stage is being discharged by discharge circuit 2100 and by the power supply. As shown, while the pulse generator stage is being discharged, the current flows from the output port OUT, through the switch 2130, through discharge resistor 2150, and to power supply terminal V2. The pulse generator stage is discharged in response to the voltage of the pulse generator stage causing current to flow through LED 2180. In response to the current, LED 2180 emits light, and in response to the light emitted by LED 2180, phototransistor 2140 turns off, causing switch 2130 to conduct current from output port OUT, through the switch 2130, through discharge resistor 2150, and to power supply terminal V2.

In some embodiments, discharge circuit stage 2100 may be used as discharge circuit 1850 of FIG. 18.

Figure 22A:
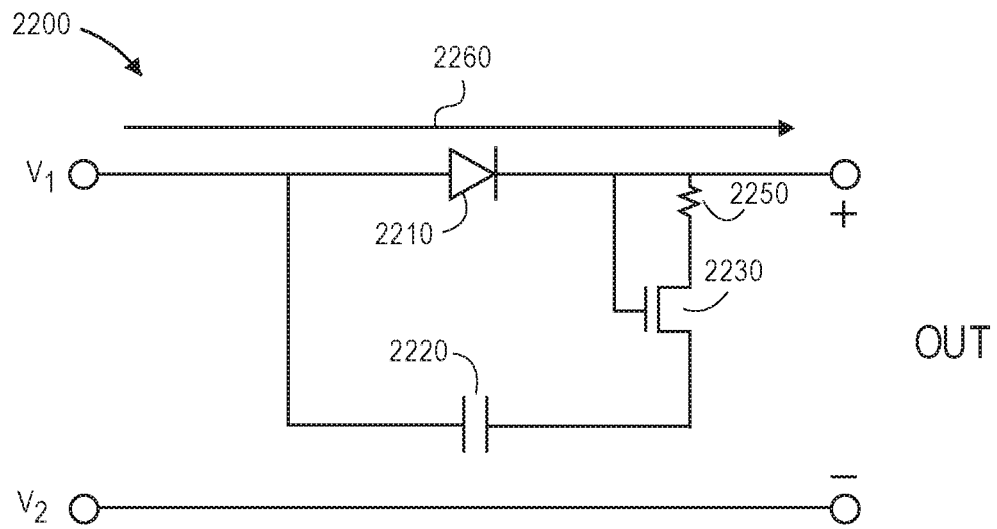
FIGS. 22A and 22B are schematic illustrations of an embodiment of a discharge circuit stage used in the pulse generator stage of FIG. 16.
Figure 22B:
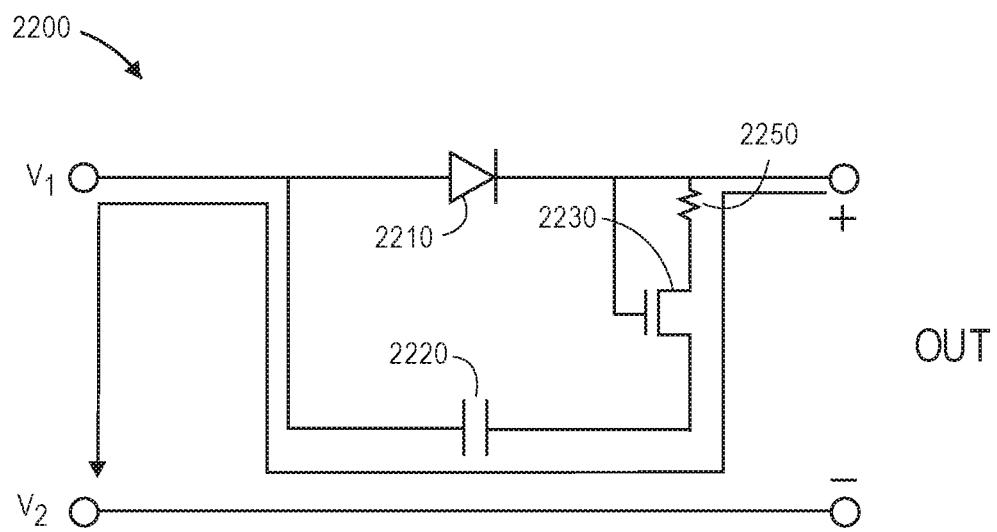

FIGS. 22A and 22B are schematic illustrations of an alternative embodiment of a discharge circuit stage 2200 used as or in a discharge circuit for a pulse generator as described herein or for pulse generators of other topologies. For example, discharge circuit stage 2200 may be used in the pulse generator stage 1600 of FIG. 16. An instance of discharge circuit stage 2200 is used to interface between each pulse generator stage and the power supply used to charge the pulse generator stages. Discharge circuit stage 2200 includes blocking diode 2210, bridge capacitor 2220, switch 2230, and discharge resistor 2250.

FIG. 22A includes an indication 2260 of the current path from the power supply to the pulse generator stage while the pulse generator stage is being charged by the power supply. As shown, while the pulse generator stage is being charged, the current flows from the power supply through blocking diode 2210, to the output port OUT, and to the pulse generator stage being charged (not shown). The pulse generator stage is charged in response to the power supply input voltage being greater than the voltage of the pulse generator stage by at least a forward voltage drop of the blocking diode 2210.

FIG. 22B includes an indication 2270 of the current path from the pulse generator stage to the power supply while the pulse generator stage is being discharged by discharge circuit 2200 and by the power supply. As shown, while the pulse generator stage is being discharged, the current flows from the output port OUT, through discharge resistor 2250, through the switch 2230, and to power supply terminal V1. The pulse generator stage is discharged in response to the voltage of the pulse generator stage exceeding the power supply input voltage by at least a threshold voltage of the switch 2230. In response to the voltage of the pulse generator stage exceeding the power supply input voltage by at least a threshold voltage of the switch 2230, switch 2230 becomes conductive.

In some embodiments, discharge circuit stage 2200 may be used as discharge circuit 1850 of FIG. 18.

Figure 23A:
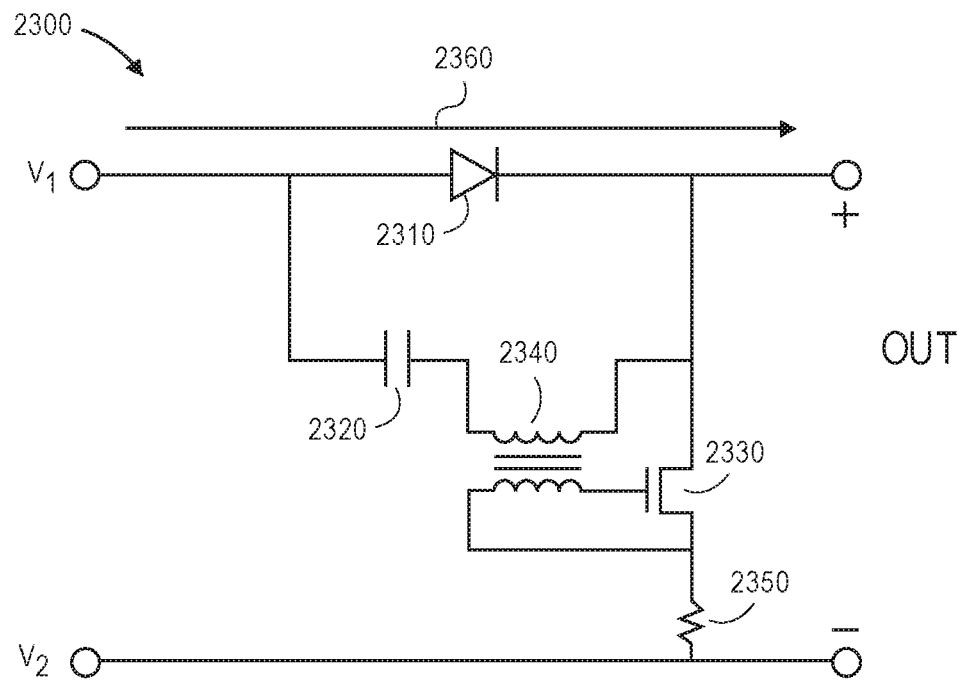
FIGS. 23A and 23B are schematic illustrations of an embodiment of a discharge circuit stage used in the pulse generator stage of FIG. 16.
Figure 23B:
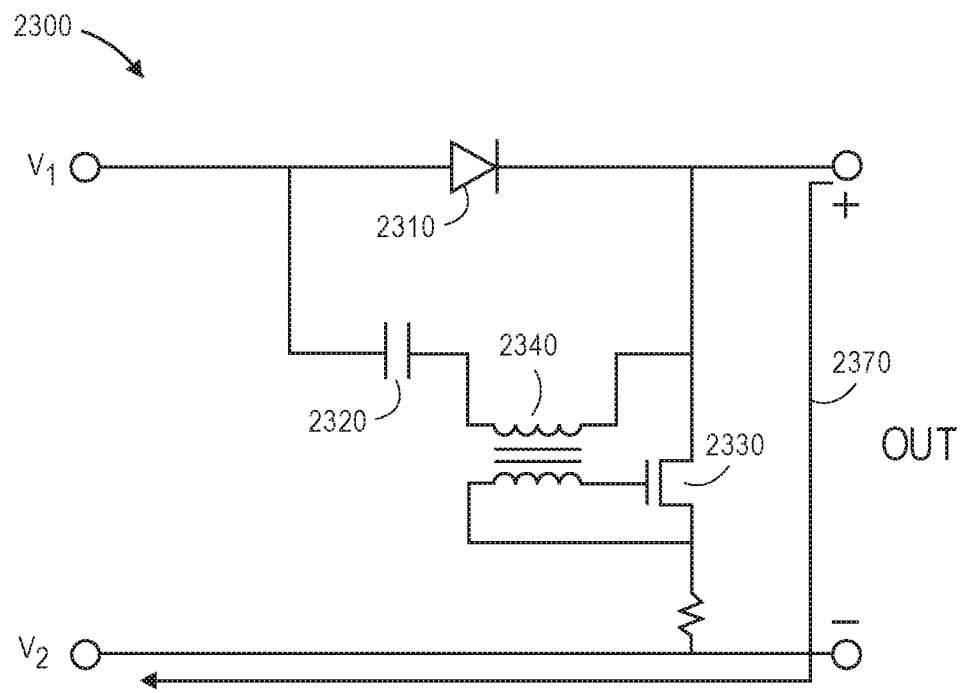

FIGS. 23A and 23B are schematic illustrations of an alternative embodiment of a discharge circuit stage 2300 which may be used as or in a discharge circuit for a pulse generator as described herein or for pulse generators of other topologies. For example, discharge circuit stage 2000 may be used in the pulse generator stage 1700 of FIG. 16. An instance of discharge circuit stage 2300 is used to interface between each pulse generator stage and the power supply used to charge the pulse generator stages. Discharge circuit stage 2300 includes blocking diode 2310, bridge capacitor 2320, switch 2330, transformer 2340, and discharge resistor 2350.

FIG. 23A includes an indication 2360 of the current path from the power supply to the pulse generator stage while the pulse generator stage is being charged by the power supply. As shown, while the pulse generator stage is being charged, the current flows from the power supply through blocking diode 2310, to the output port OUT, and to the pulse generator stage being charged (not shown). The pulse generator stage is charged in response to the power supply input voltage being greater than the voltage of the pulse generator stage by at least a forward voltage drop of the blocking diode 2310.

FIG. 23B includes an indication 2370 of the current path from the pulse generator stage to the power supply while the pulse generator stage is being discharged by discharge circuit 2300 and by the power supply. As shown, while the pulse generator stage is being discharged, the current flows from the output port OUT, through the switch 2330, through discharge resistor 2350, and to power supply terminal V2. The pulse generator stage is discharged in response to the voltage of the power supply input voltage dropping to a voltage less than the voltage of the pulse generator stage. This causes a current to flow through the primary inductor of transformer 2340, which induces a voltage across the gate and source of switch 2330 causing switch 2330 to conduct current from the output port OUT, through the switch 2330, through discharge resistor 2350, and to power supply terminal V2.

In some embodiments, discharge circuit stage 2300 may be used as discharge circuit 1850 of FIG. 18.

Figure 24:
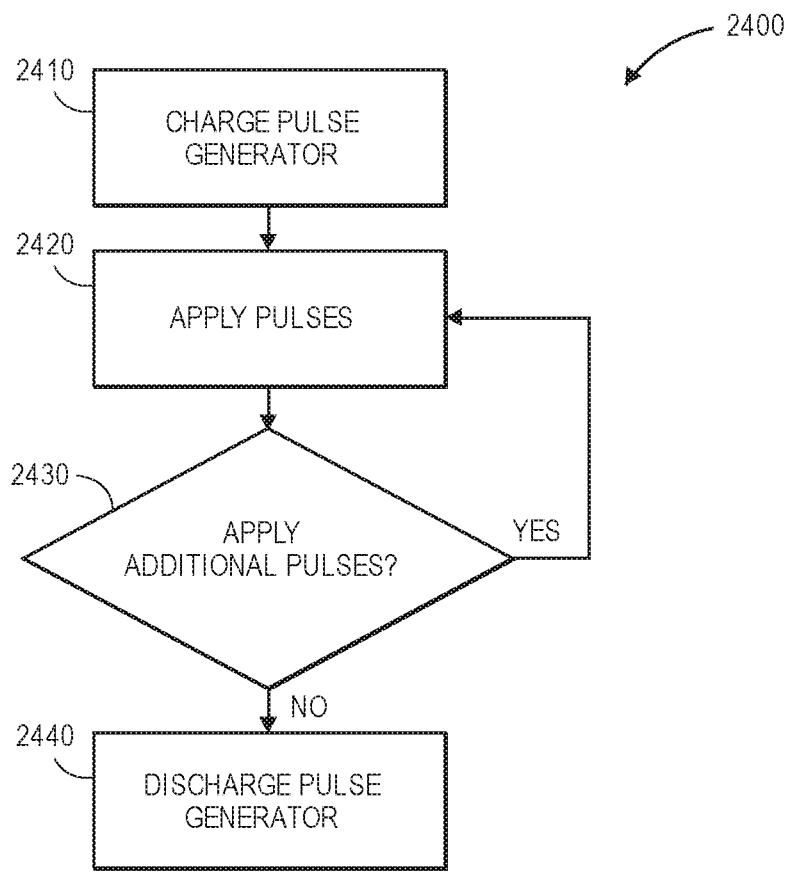
FIG. 24 is a flowchart diagram illustrating a method of using a pulse generator system.

FIG. 24 is a flowchart diagram illustrating a method 2400 of using a pulse generator system, such as embodiments of pulse generator systems discussed herein which include discharge circuitry. The method 2400 may be used with or as part of any of the methods discussed in U.S. patent application Ser. No. 15/148,344, filed May 6, 2016, and titled "HIGH-VOLTAGE ANALOG CIRCUIT PULSER WITH FEEDBACK CONTROL," which is incorporated herein by reference.

At 2410, a pulse generator circuit of the pulse generator system is charged. For example, the pulse generator system may be charged by charging the capacitors of a pulse generator circuit, for example, as discussed above with reference to capacitors 515, 525, and 535 of FIG. 6A.

At 2420, pulses are generated and applied to a patient or a test subject. For example, electrodes of the pulse generator system may be used to discharge the pulse generator circuit in order to apply pulses to a patient or at test subject, for example, as discussed above with reference to FIG. 6B.

At 2430, a determination is made regarding whether additional pulses are to be applied to the patient or the test subject. If additional pulses are to be applied, the method returns to 2420, and additional pulses are applied. If additional pulses are not to be applied, the method continues to 2440.

At 2440, the pulse generator circuit of the pulse generator system is discharged. For example, the pulse generator circuit may be discharged using a discharge circuit, such as that discussed elsewhere herein. For example, if additional pulses are not to be applied to the patient or test subject, the input voltage may be turned off and the pulse generator circuit of the pulse generator system may be discharged such that the voltage across the energy storage capacitors of the pulse generator circuit is less than 100 V, 50 V, 20 V, 10 V, 5 V, or 1 V, where the energy storage capacitors had been previously charged to a voltage greater than 1000 V, 2500 V, or 5000 V.

Accordingly, by including the discharge circuit, the nsPEF pulse generator is more safe. The nsPEF pulse generator may be fully charged only after an impedance or initial safety check passes and can automatically be discharged immediately after pulsing ends. This eliminates the chances of mistakenly applying high voltage to the patient or a user.

Figure 25:
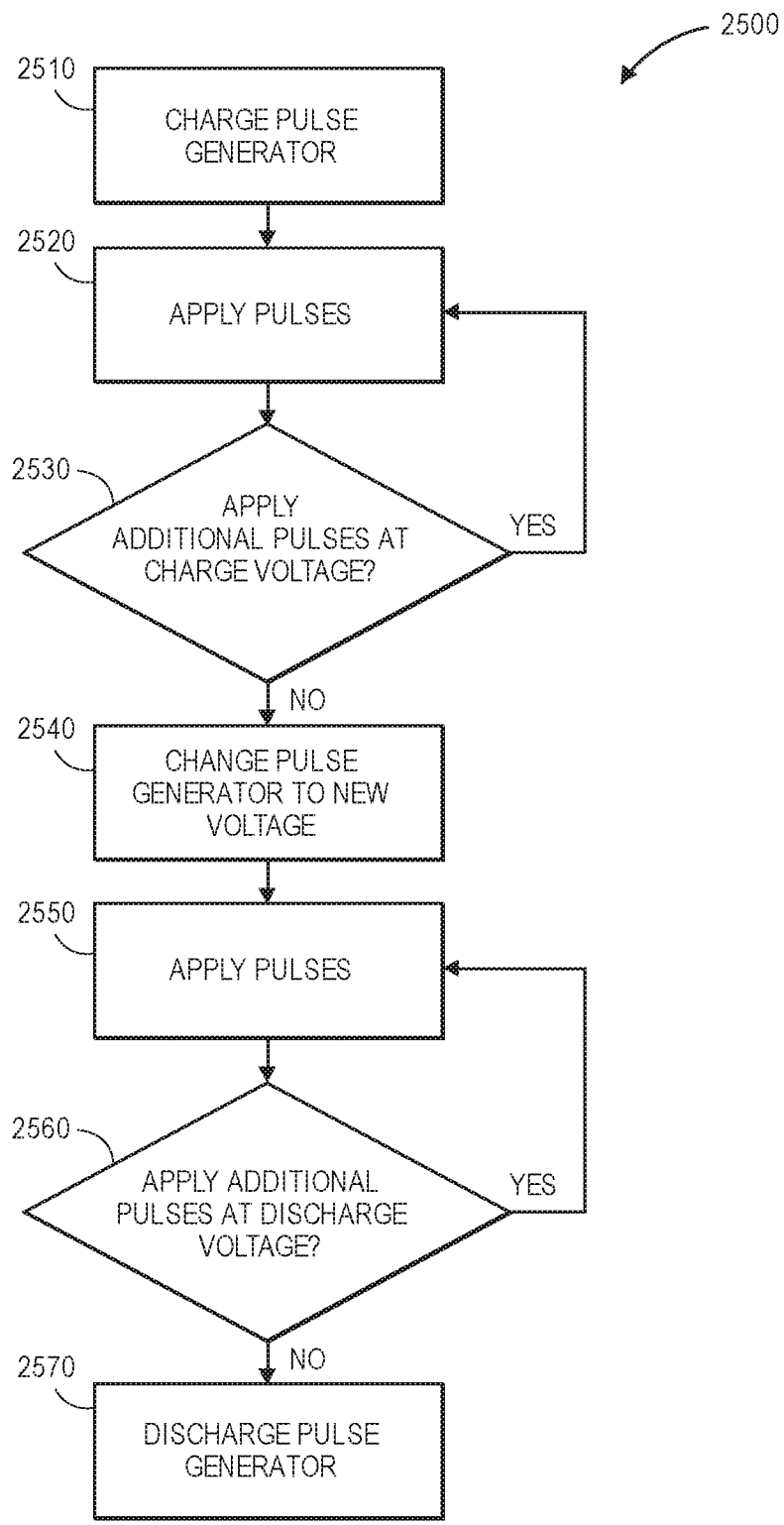
FIG. 25 is a flowchart diagram illustrating a method of using a pulse generator system.

FIG. 25 is a flowchart diagram illustrating a method 2500 of using a pulse generator system, such as embodiments of pulse generator systems discussed herein which include discharge circuitry. The method 2500 may be used with or as part of any of the methods discussed in U.S. patent application Ser. No. 15/148,344, filed May 6, 2016, and titled "HIGH-VOLTAGE ANALOG CIRCUIT PULSER WITH FEEDBACK CONTROL," which is incorporated herein by reference.

At 2510, a pulse generator circuit of the pulse generator system is charged. For example, the pulse generator system may be charged by charging a pulse generator circuit, for example, as discussed above with reference to FIG. 6A.

At 2520, pulses are generated and applied to a patient or a test subject. For example, electrodes of the pulse generator system may be used to discharge the pulse generator circuit in order to apply pulses to a patient or at test subject, for example, as discussed above with reference to FIG. 6B.

At 2530, a determination is made regarding whether additional pulses corresponding to the voltage of the charging of 2510 are to be applied to the patient or the test subject. If additional pulses corresponding to the voltage of the charging of 2510 are to be applied, the method returns to 2520, and additional pulses are applied. If additional pulses are not to be applied, the method continues to 2540.

At 2540, the voltage of the pulse generator circuit of the pulse generator system is changed, for example, is discharged to a voltage less than the voltage of the charging of 2510. For example, the pulse generator system may be discharged using a discharge circuit, such as those discussed herein. For example, the pulse generator circuit of the pulse generator system may be discharged from a voltage of 5000 V to a discharge voltage of 4000 V.

At 2550, pulses are generated and applied to a patient or a test subject. For example, electrodes of the pulse generator system may be used to discharge the pulse generator circuit in order to apply pulses to a patient or at test subject, for example, as discussed above with reference to FIG. 6B.

At 2560, a determination is made regarding whether additional pulses corresponding to the voltage of the discharging of 2540 are to be applied to the patient or the test subject. If additional pulses corresponding to the voltage of the discharging of 2540 are to be applied, the method returns to 2550, and additional pulses are applied. If additional pulses are not to be applied, the method continues to 2570.

At 2570, the pulse generator circuit of the pulse generator system is discharged from the discharge voltage. For example, the pulse generator circuit may be discharged using a discharge circuit, such as that discussed elsewhere herein. For example, if additional pulses are not to be applied to the patient or test subject, the pulse generator circuit of the pulse generator system may be discharged such that the voltage across the energy storage capacitors of the pulse generator circuit is less than 100 V, 50 V, 20 V, 10 V, 5 V, or 1 V, where the energy storage capacitors had been previously charged to a voltage greater than 1000 V, 2500 V, 4000 V, or 5000 V.

Figure 26:
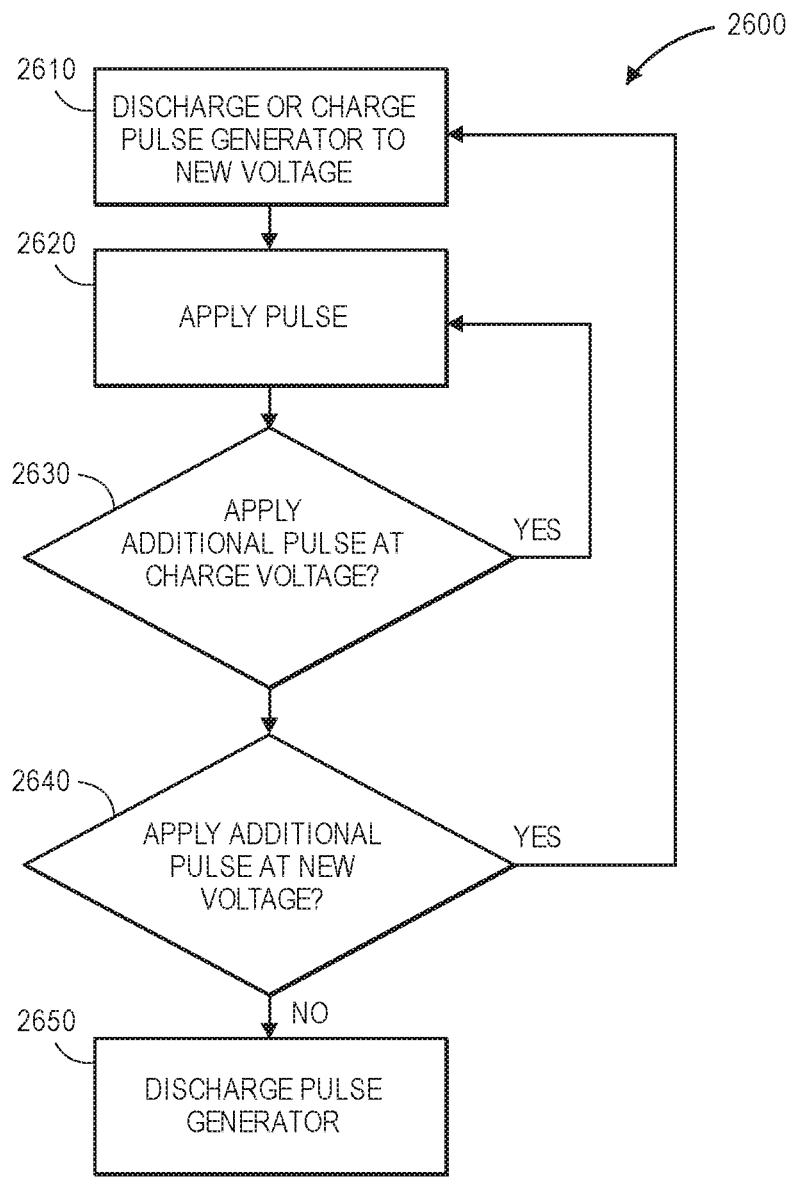
FIG. 26 is a flowchart diagram illustrating a method of using a pulse generator system.

FIG. 26 is a flowchart diagram illustrating a method 2600 of using a pulse generator system, such as embodiments of pulse generator systems discussed herein which include discharge circuitry. The method 2600 may be used with or as part of any of the methods discussed in U.S. patent application Ser. No. 15/148,344, filed May 6, 2016, and titled "HIGH-VOLTAGE ANALOG CIRCUIT PULSER WITH FEEDBACK CONTROL," which is incorporated herein by reference.

At 2610, a pulse generator circuit of the pulse generator system is charged or discharged to a new voltage. For example, the pulse generator system may be charged by charging a pulse generator circuit, for example, as discussed above with reference to FIG. 6A. Alternatively, the pulse generator system may be discharged by discharging a pulse generator circuit with a discharge circuit, such as that discussed above with reference to FIG. 17.

At 2630, a determination is made regarding whether an additional pulse corresponding to the voltage of the charging or discharging of 2610 is to be applied to the patient or the test subject. If an additional pulse corresponding to the voltage of the charging or discharging of 2610 is to be applied, the method returns to 2620, and an additional pulse is applied. If an additional pulse is not to be applied, the method continues to 2640.

At 2640, a determination is made regarding whether an additional pulse corresponding to a new voltage is to be applied to the patient or the test subject. If an additional pulse corresponding to a new voltage is to be applied, the method returns to 2610, and the pulse generator circuit of the pulse generator system is charged or discharged to a new voltage. In response to a determination that an additional pulse is not is not to be applied, the method continues to 2650.

At 2650, the pulse generator circuit of the pulse generator system is discharged from its previous voltage. For example, if additional pulses are not to be applied to the patient or test subject, the pulse generator circuit of the pulse generator system may be discharged such that the voltage across the energy storage capacitors of the pulse generator circuit is less than 100 V, 50 V, 20 V, 10 V, 5 V, or 1 V, where the energy storage capacitors had been previously charged or discharged to a voltage greater than 1000 V, 2500 V, 4000 V, or 5000 V.

Accordingly, using the method 2600, the voltage for each next applied pulse may be increased or decreased after each pulse is applied or may be increased or decreased after each predetermined number of pulses are applied. In some embodiments, a voltage for each next pulse is determined, and the pulse generator system is charged or discharged accordingly.

Applying nsPEF to a tumor sufficient to stimulate apoptosis includes at least the electrical characteristics found experimentally. For example, a 100 ns long pulse with a 20 ns rise time to 30 kV/cm (kilovolts per centimeter) at 1 to 7 pulses per second (pps) for 500 to 2000 pulses has been found to be sufficient to stimulate apoptosis, depending on the tumor type. Pulsed electric fields of at least 20 kV/cm have been shown to be effective. A number of pulses greater than 50 pulses has also been shown to be effective. Current values between 12 A and 60 A resulted, depending on the electrode type and skin resistance.

The embodiments of pulse generators described herein have many uses. Cancer that has metastasized through a subject's bloodstream may be treated using nsPEF's immune stimulation properties. For treatment, circulating tumor cells (CTCs) are isolated from the bloodstream and amassed in vial, test tube, or other suitable in vitro environment. In some cases, there may only be a few (e.g., 5, 10), tumor cells that are collected and amassed. Through this mass, an nsPEF electric field is applied in order to treat the cells. This may cause calreticulin or one or more other damage-associated molecular patterns (DAMPs) to be expressed on the surface membranes of the tumor cells. The tumor cells may then be introduced back into the subject's bloodstream by injection, infusion, or otherwise.

In an alternative embodiment, single CTCs may also be isolated from the bloodstream, and each tumor cell treated individually. An automated system that captures CTCs in whole blood using iron nanoparticles coated with a polymer layer carrying biotin analogues and conjugated with antibodies for capturing CTCs can automatically capture the tumor cells, and a magnet and or centrifuge can separate them. After separation from the antibodies, the CTCs may be treated with nsPEF through a small capillary and then reintroduced to the patient's bloodstream.

While examples in the application discuss human and murine subjects, the treatment of other animals is contemplated. Agricultural animals, such as horses and cows, or racing animals, such as horses, may be treated. Companion animals, such as cats and dogs, may find special use with the treatments described herein. It may be difficult for a veterinarian to remove many tumors from a small animal, and cancers may be caught relatively late because the animals cannot communicate their advancing pain. Further, the risk inherent in reinjecting tumor cells—albeit treated tumor cells—may be worth the potential benefits of potentially halting a metastasized cancer in a loved pet.

The methods of the present invention can be used for the treatment of any type of cancer, whether characterized as malignant, benign, soft tissue, or solid, and cancers of all stages and grades including pre- and post-metastatic cancers. Examples of different types of cancer include, but are not limited to, digestive and gastrointestinal cancers such as gastric cancer (e.g., stomach cancer), colorectal cancer, gastrointestinal stromal tumors, gastrointestinal carcinoid tumors, colon cancer, rectal cancer, anal cancer, bile duct cancer, small intestine cancer, and esophageal cancer; breast cancer; lung cancer; gallbladder cancer; liver cancer; pancreatic cancer; appendix cancer; prostate cancer, ovarian cancer; renal cancer (e.g., renal cell carcinoma); cancer of the central nervous system; skin cancer (e.g., melanoma); lymphomas; gliomas; choriocarcinomas; head and neck cancers; osteogenic sarcomas; and blood cancers.

Electrical characteristics of nsPEF treatments can be adjusted based on a size and/or a type of a tumor. Types of tumors may include tumors of different regions of the body, such as the cancerous tumors described above.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

The above description is illustrative and is not restrictive. Many variations of the invention will become apparent to those skilled in the art upon review of the disclosure. The scope of the invention should, therefore, be determined not with reference to the above description, but instead should be determined with reference to the pending claims along with their full scope or equivalents.

As noted previously, all measurements, dimensions, and materials provided herein within the specification or within the figures are by way of example only.

A recitation of "a," "an," or "the" is intended to mean "one or more" unless specifically indicated to the contrary. Reference to a "first" component does not necessarily require that a second component be provided. Moreover reference to a "first" or a "second" component does not limit the referenced component to a particular location unless expressly stated.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

What is claimed is:

1. A method of generating high voltage pulses, the method comprising:
   receiving, by a driver circuit, input signal pulses;
   generating, by the driver circuit, driving signal pulses based on the input signal pulses; and
   generating, at a plurality of serially connected pulse generator stages and based on the driving signal pulses, output pulses that have a higher amplitude than the driving signal pulses by:
     charging a capacitive element in a respective pulse generator stage; and
     generating, by at least one switch driver, control signal pulses configured to switch a plurality of switches to discharge the capacitive element, the plurality of switches are connected in series to form a switch stack,
   wherein an input port of the at least one switch driver is coupled to an output port of the driver circuit, an output port of the at least one switch driver is coupled to a respective switch of the plurality of switches; and
   wherein the input port of the at least one switch driver is coupled to the output port of the at least one switch driver through a transformer.

2. The method of claim 1, wherein the plurality of pulse generator stages comprises five or fewer stages.

3. The method of claim 1, wherein a maximum width of the control signal pulses, a maximum turn-on time of the plurality of switches, and a maximum pulse width of the output pulses are within a nanosecond range.

4. The method of claim 1, further comprising:
   selectively discharging a pulse generator stage of the plurality of serially connected pulse generator stages based on a difference between a charging voltage and a voltage across the capacitive element in the pulse generator stage.

5. The method of claim 4, wherein selectively discharging the pulse generator stage comprises discharging the capacitive element by a discharge switch stack through a discharge resistor.

6. The method of claim 1, wherein at least some of the plurality of pulse generator stages generate the output pulses having an amplitude of 5 kV or greater.

7. The method of claim 1, further comprising delivering the generated output pulses with a set of electrodes.

8. The method of claim 1, wherein at least some of the plurality of the pulse generator stages comprises a Marx generator.

9. The method of claim 1, wherein all of the plurality of switches of the switch stack are turned on and turned off substantially simultaneously.

10. The method of claim 1, wherein the method is used for treatment of a tumor.

11. The method of claim 10, wherein the tumor is cancerous, precancerous, or benign.

12. The method of claim 10, comprising adjusting characteristics of the output pulses based on a size and/or a type of the tumor.

13. The method of claim 1, wherein the transformer comprises a lossy transformer.

14. The method of claim 1, further comprising increasing or decreasing a charging voltage of a power supply after an output pulse of the output pulses or after a predetermined number of the output pulses.

15. The method of claim 1, further comprising:
   discharging, using a discharge circuit, one or more of the plurality of pulse generator stages to a discharge voltage.

16. The method of claim 15, the method further comprising applying the output pulses to a patient or a test subject, wherein the discharging the one or more of the plurality of pulse generator stages comprises discharging each of the plurality of pulse generator stages to stop applying the output pulses to the patient or the test subject.

17. The method of claim 15, wherein the discharging the one or more of the plurality of pulse generator stages comprises discharging the one or more of the plurality of pulse generator stages to a lower voltage to apply the output pulses to a patient or a test subject.

18. A method of generating high voltage pulses, the method comprising:
   receiving, by a driver circuit, input signal pulses;
   generating, by the driver circuit, driving signal pulses based on the input signal pulses;
   generating, at a plurality of pulse generator stages and based on the driving signal pulses, output pulses that have a higher amplitude than the driving signal pulses by:
     charging a capacitive element in a respective pulse generator stage of the plurality of pulse generator stages; and
     generating, by at least one switch driver, control signal pulses configured to switch a plurality of switches to discharge the capacitive element to generate at least a portion of an output pulse of the output pulses, wherein the plurality of switches are connected in series to form a switch stack,
     wherein an input port of the at least one switch driver is coupled to an output port of the driver circuit, an output port of the at least one switch driver is coupled to a respective switch of the plurality of switches, and wherein the input port of the at least one switch driver is coupled to the output port of the at least one switch driver through a transformer; and
   selectively discharging, with a discharge circuit, one or more pulse generator stages of the plurality of pulse generator stages to a discharge voltage.

19. The method of claim 18, the method comprising dropping voltage of a power supply to a voltage less than a voltage of the one or more of the plurality of pulse generator stages.

20. The method of claim 19, wherein the selectively discharging comprises selectively discharging in response to charging voltage of the power supply dropping to the voltage less than the voltage of the one or more of the plurality of pulse generator stages.

21. The method of claim 18, wherein the selectively discharging the one or more of the plurality of pulse generator stages comprises discharging each of the plurality of pulse generator stages, wherein the discharge voltage is less than 100 volts.

22. The method of claim 18, wherein the charging the capacitive element in the respective pulse generator stage comprises charging the capacitive element to a first charging voltage, wherein the discharge voltage is a second charging voltage lower than the first charging voltage, and wherein the selectively discharging the one or more of the plurality of pulse generator stages comprises discharging the one or more of the plurality of pulse generator stages to the second charging voltage to continue applying the output pulses.

23. The method of claim 18, further comprising:
receiving, at the discharge circuit, a discharge signal, wherein the selectively discharging the one or more of the plurality of pulse generator stages is in response to the discharge signal.

\* \* \* \* \*